(12) United States Patent
Lachia et al.

(10) Patent No.: US 8,946,280 B2
(45) Date of Patent: Feb. 3, 2015

(54) PLANT GROWTH REGULATING COMPOUNDS

(75) Inventors: Mathilde Denise Lachia, Basel (CH); Alain De Mesmaeker, Stein (CH); Hanno Christian Wolf, Stein (CH); Pierre Joseph Marcel Jung, Stein (CH)

(73) Assignee: Syngenta Participations AG, Basel (CH)

( * ) Notice: Subject to any disclaimer, the term of this patent is extended or adjusted under 35 U.S.C. 154(b) by 43 days.

(21) Appl. No.: 13/994,204

(22) PCT Filed: Dec. 9, 2011

(86) PCT No.: PCT/EP2011/072303
§ 371 (c)(1),
(2), (4) Date: Jul. 5, 2013

(87) PCT Pub. No.: WO2012/080115
PCT Pub. Date: Jun. 21, 2012

(65) Prior Publication Data
US 2013/0303375 A1 Nov. 14, 2013

(30) Foreign Application Priority Data

Dec. 14, 2010 (GB) .................................. 1021224.9
Aug. 4, 2011 (GB) .................................. 1113516.7

(51) Int. Cl.
| | | |
|---|---|---|
| *C07D 209/70* | (2006.01) |
| *A01N 43/40* | (2006.01) |
| *C07D 401/04* | (2006.01) |
| *C07D 405/12* | (2006.01) |
| *C07D 405/14* | (2006.01) |
| *C07D 417/04* | (2006.01) |
| *C07D 417/14* | (2006.01) |
| *A01N 43/90* | (2006.01) |
| *A01N 43/38* | (2006.01) |
| *C07D 209/94* | (2006.01) |
| *C07D 471/04* | (2006.01) |
| *C07D 491/052* | (2006.01) |

(52) U.S. Cl.
CPC .............. *A01N 43/90* (2013.10); *C07D 209/70* (2013.01); *C07D 401/04* (2013.01); *C07D 405/12* (2013.01); *C07D 405/14* (2013.01); *C07D 417/04* (2013.01); *C07D 417/14* (2013.01); *A01N 43/38* (2013.01); *A01N 43/40* (2013.01); *C07D 209/94* (2013.01); *C07D 471/04* (2013.01); *C07D 491/052* (2013.01)

USPC ........ 514/411; 514/461; 514/473; 504/116.1; 504/189; 504/221; 504/222; 504/284; 504/287; 548/427; 548/429; 548/450; 549/315

(58) Field of Classification Search
USPC .............. 504/116.1, 189, 221, 222, 284, 287; 548/427, 429, 450; 549/315; 514/411, 514/461, 473

See application file for complete search history.

(56) References Cited

FOREIGN PATENT DOCUMENTS

| | | |
|---|---|---|
| WO | 2009/138655 | 11/2009 |
| WO | WO 2009138655 A2 * | 11/2009 |

OTHER PUBLICATIONS

A. W. Johnson et al., The Preparation of Synthetic Analogues of Strigol, 1981, Journal of the Chemical Society, Perkin Transactions I, GB, No. 6, pp. 1734-1743.*
International Search Report, International Application No. PCT/EP2011/072303, completion date: Jan. 10, 2012.
Johnsson A W et al: "The Preparation of Synthetic Analogues of Strigol", Journal of the Chemical Society, Perkin Transactions 1, Chemical Society, Letchworth; GB, No. 6, Jan. 1, 1981, pp. 1734-1743.

* cited by examiner

*Primary Examiner* — Jane C Osweckí
(74) *Attorney, Agent, or Firm* — R. Kody Jones

(57) ABSTRACT

The present invention relates to novel strigolactam derivatives of formula (I) to processes and intermediates for preparing them, to plant growth regulator compositions comprising them and to methods of using them for controlling the growth of plants and/or promoting the germination of seeds.

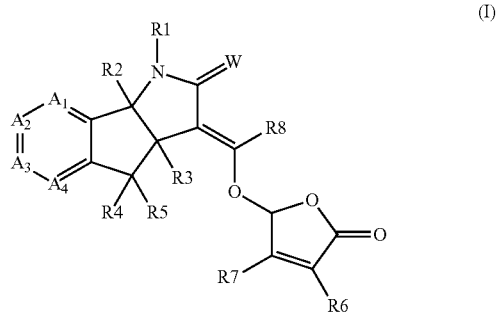

9 Claims, No Drawings

PLANT GROWTH REGULATING COMPOUNDS

This application is a 371 of International Application No. PCT/EP2011/072303 filed Dec. 9, 2011, which claims priority to EP 1021224.9 filed Dec. 14, 2010, and 1113516.7 filed Aug. 4, 2011, the contents of which are incorporated herein by reference.

The present invention relates to novel strigolactam derivatives, to processes and intermediates for preparing them, to plant growth regulator compositions comprising them and to methods of using them for controlling the growth of plants and/or promoting the germination of seeds.

Strigolactone derivatives are phytohormones with plant growth regulation and seed germination properties; they have been described, for example, in WO2009/138655, WO2010/125065, WO05/077177, WO06/098626, and Annual Review of Phytopathology (2010), 48 p. 93-117. Strigolactone derivatives, like the synthetic analogue GR24, are known to have effect on the germination of parasitic weeds, such as *Orobanche* species. It is well established in the art that testing for germination of *Orobanche* seeds is a useful test to identify strigolactone analogues (for example, see Plant and Cell Physiology (2010), 51(7) p. 1095; and Organic & Biomolecular Chemistry (2009), 7(17), p. 3413).

It has now surprisingly been found that certain strigolactam derivatives have properties analogous to strigolactone.

According to the present invention, there is provided a compound of formula (I)

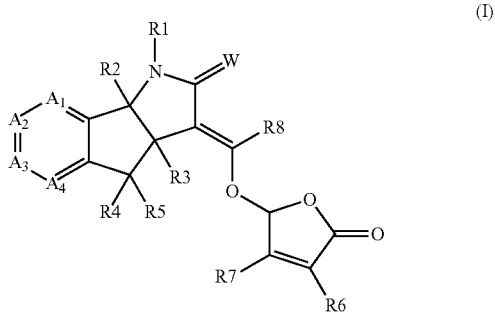

(I)

wherein
W is O or S;
R2 and R3 are independently hydrogen, or C1-C3 alkyl;
R4 and R5 are independently hydrogen, halogen, nitro, cyano, C1-C3 alkyl, C1-C3 haloalkyl, C1-C3 alkoxy, hydroxyl, —OC(O)R9, amine, N—C1-C3 alkyl amine, or N,N-di-C1-C3 alkyl amine;
R9 is hydrogen, C1-C6 alkyl, C1-C6 alkoxy, or C1-C6 haloalkyl;
R6 and R7 are independently hydrogen, C1-C3 alkyl, hydroxyl, or C1-C3 alkoxy;
R8 is hydrogen, nitro, cyano, C1-C6 alkyl, or C1-C6 haloalkyl;
R1 is hydrogen, C1-C6 alkoxy, hydroxyl, amine, N—C1-C6 alkyl amine, N,N-di-C1-C6 alkyl amine, C1-C6 alkyl optionally substituted by one to five R10, C1-C8 alkylcarbonyl, C1-C8 alkoxycarbonyl, aryl, aryl substituted by one to five R10, heteroaryl, heteroaryl substituted by one to five R10, heterocyclyl, heterocyclyl substituted by one to five R10, benzyl, or benzyl substituted by one to five R10;
R10 is hydrogen, cyano, nitro, halogen, C1-C6 alkyl, C1-C6 alkoxy, C1-C6 haloalkyl, C2-C6 alkenyl, or C2-C6 alkynyl;
$A_1, A_2, A_3$ and $A_4$ are each independently C—X or nitrogen, wherein each X may be the same or different, and provided that no more than two of $A_1, A_2, A_3$ and $A_4$ are nitrogen;
and X is hydrogen, halogen, cyano, hydroxyl, —OC(O)R9, C1-C6 alkoxy, C1-C6 alkyl, C1-C6 haloalkyl, C1-C3 hydroxyalkyl, nitro, amine, N—C1-C6 alkyl amine, N,N-di-C1-C6 alkyl amine, or NHC(O)R9.

The compounds of formula (I) may exist in different geometric or optical isomers (diastereoisomers and enantiomers) or tautomeric forms. This invention covers all such isomers and tautomers and mixtures thereof in all proportions as well as isotopic forms such as deuterated compounds. The invention also covers all salts, N-oxides, and metalloidic complexes of the compounds of formula (I).

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are preferably $C_1$ to $C_6$ alkyl groups, more preferably $C_1$-$C_4$ and most preferably $C_1$-$C_3$ alkyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —CF₃, —CF₂Cl, —CH₂CF₃ or —CH₂CHF₂.

Hydroxyalkyl groups are alkyl groups which are substituted with one or more hydroxyl group and are, for example, —CH₂OH, —CH₂CH₂OH or —CH(OH)CH₃.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

Unless otherwise indicated, alkenyl and alkynyl, on their own or as part of another substituent, may be straight or branched chain and may preferably contain 2 to 6 carbon atoms, preferably 2 to 4, more preferably 2 to 3, and where appropriate, may be in either the (E)- or (Z)-configuration. Examples include vinyl, allyl and propargyl.

The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyridyl, pyridazinyl, pyrimidinyl, pyrazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. A preferred heteroaryl group is pyridine.

The term "heterocyclyl" is defined to include heteroaryl and in addition their unsaturated or partially unsaturated analogues such as 4,5,6,7-tetrahydro-benzothiophenyl, 9H-fluorenyl, 3,4-dihydro-2H-benzo-1,4-dioxepinyl, 2,3-dihydrobenzofuranyl, piperidinyl, 1,3-dioxolanyl, 1,3-dioxanyl, 4,5-dihydro-isoxazolyl, tetrahydrofuranyl and morpholinyl.

Preferred values of W, R2, R3, R4, R5, R9, R8, R1, R10, $A_1, A_2, A_3, A_4$ and X are, in any combination, as set out below.
W is preferably oxygen.
R2 is preferably hydrogen, methyl, or ethyl; most preferably R2 is hydrogen.
R3 is preferably hydrogen, methyl, or ethyl; most preferably R3 is hydrogen.
R4 is preferably hydrogen, hydroxyl, methyl, or ethyl; most preferably R4 is hydrogen or hydroxyl.

R5 is preferably hydrogen, hydroxyl, methyl, or ethyl; most preferably R5 is hydrogen or hydroxyl.
R6 is preferably hydrogen, methyl, or ethyl; most preferably R6 is methyl.
R7 is preferably hydrogen, methyl, or ethyl; most preferably R7 is hydrogen.
R8 is preferably hydrogen, methyl, or ethyl; most preferably R8 is hydrogen.
R1 is preferably hydrogen, C1-C6 alkoxy, C1-C6 alkyl substituted or not by one to five R10, C1-C8 alkylcarbonyl, C1-C8 alkoxycarbonyl, aryl, aryl substituted by one to five R10, heteroaryl, heteroaryl substituted by one to five R10, heterocyclyl, heterocyclyl substituted by one to five R10, benzyl, or benzyl substituted by one to five R10; more preferably R1 is hydrogen, C1-C6 alkoxy, C1-C6 alkyl substituted or not by one to five R10, C1-C8 alkylcarbonyl, C1-C8 alkoxycarbonyl, benzyl, or benzyl substituted by one to five R10; most preferably R1 is hydrogen, methyl, ethyl, phenyl, benzyl, acetate, or methoxycarbonyl.
R10 is independently hydrogen, cyano, nitro, halogen, C1-C6 alkyl, C1-C6 alkoxy, C1-C6 haloalkyl; most preferably R10 is hydrogen, cyano, nitro, chloride, bromine, fluorine, methyl, methoxy and trifluoromethyl.
Preferably $A_1$ is C—X.
Preferably $A_2$ is C—X.
Preferably $A_3$ is C—X.
Preferably $A_4$ is C—X.
Preferably, X is hydrogen, hydroxyl, halogen, cyano, methyl, ethyl, n-propyl, hydroxymethyl, trifluoromethyl or methoxy. More preferably, X is hydrogen, hydroxyl, methyl, trifluoromethyl or methoxy. Even more preferably, X is hydrogen, methyl, hydroxyl or methoxy. Most preferably, X is hydrogen, methyl, hydroxyl or methoxy.
In a preferred embodiment, there is provided a compound of formula (I) wherein
W is O;
R2 and R3 are independently hydrogen, methyl or ethyl;
R4 and R5 are independently hydrogen, hydroxyl, methyl or ethyl;
R6, R7 and R8 are independently hydrogen, methyl or ethyl;
R1 is hydrogen, C1-C6 alkoxy, C1-C6 alkyl substituted or not by one to five R10, C1-C8 alkylcarbonyl, C1-C8 alkoxycarbonyl, aryl, aryl substituted by one to five R10, heteroaryl, heteroaryl substituted by one to five R10, heterocyclyl, heterocyclyl substituted by one to five R10, benzyl, or benzyl substituted by one to five R10;
R10 is independently hydrogen, cyano, nitro, halogen, C1-C6 alkyl, C1-C6 alkoxy or C1-C6 haloalkyl;
$A_1, A_2, A_3$ and $A_4$ are each independently C—X; and
X is hydrogen, hydroxyl, halogen, cyano, methyl, ethyl, n-propyl, hydroxymethyl, trifluoromethyl or methoxy.
In a preferred embodiment there is provided a compound is of Formula (II)

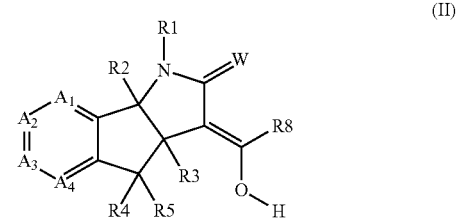

wherein
W is O or S;
R2 and R3 are independently hydrogen, or C1-C3 alkyl;
R4 and R5 are independently hydrogen, halogen, nitro, cyano, C1-C3 alkyl, C1-C3 haloalkyl, C1-C3 alkoxy, hydroxyl, —OC(O)R9, amine, N—C1-C3 alkyl amine, or N,N-di-C1-C3 alkyl amine;
R8 is hydrogen, nitro, cyano, C1-C6 alkyl, or C1-C6 haloalkyl;
R1 is hydrogen, C1-C6 alkoxy, hydroxyl, amine, N—C1-C6 alkyl amine, N,N-di-C1-C6 alkyl amine, C1-C6 alkyl optionally substituted by one to five R10, C1-C8 alkylcarbonyl, C1-C8 alkoxycarbonyl, aryl, aryl substituted by one to five R10, heteroaryl, heteroaryl substituted by one to five R10, heterocyclyl, heterocyclyl substituted by one to five R10, benzyl, or benzyl substituted by one to five R10;
R10 is hydrogen, cyano, nitro, halogen, C1-C6 alkyl, C1-C6 alkoxy, C1-C6 haloalkyl, C2-C6 alkenyl, or C2-C6 alkynyl;
$A_1, A_2, A_3$ and $A_4$ are each independently C—X or nitrogen, wherein each X may be the same or different, and provided that no more than two of $A_1, A_2, A_3$ and $A_4$ are nitrogen;
and X is hydrogen, halogen, cyano, hydroxyl, —OC(O)R9, C1-C6 alkoxy, C1-C6 alkyl, C1-C6 haloalkyl, C1-C3 hydroxyalkyl, nitro, amine, N—C1-C6 alkyl amine, N,N-di-C1-C6 alkyl amine, or NHC(O)R9;
or salts or N-oxides thereof.
The preferences for $A_1, A_2, A_3, A_4$, R1, R2, R3, R4, R5, R8 and W are the same as the preferences set out for the corresponding substituents of the compounds of the formula (I). The compound of formula (II) is an intermediate in the synthesis of the compound of formula (I).
Tables 1 to 2 below include examples of compounds of the present invention.

TABLE 1

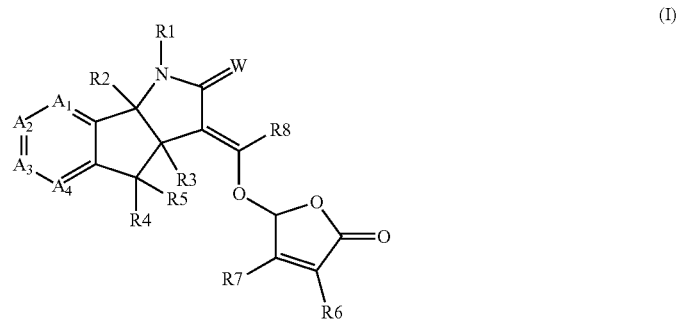

| Compound | R1 | R2 | R3 | R4 | R5 | R6 | R7 | R8 | W | $A_1$ | $A_2$ | $A_3$ | $A_4$ |
|---|---|---|---|---|---|---|---|---|---|---|---|---|---|
| 1.00 | H | H | H | H | H | CH$_3$ | H | H | O | C—H | C—H | C—H | C—H |
| 1.01 | H | H | H | OH | H | CH$_3$ | H | H | O | C—H | C—H | C—H | C—H |
| 1.02 | H | H | H | H | H | CH$_3$ | H | H | O | C—CH$_3$ | C—H | C—H | C—CH$_3$ |

TABLE 1-continued (I)

| Compound | R1 | R2 | R3 | R4 | R5 | R6 | R7 | R8 | W | $A_1$ | $A_2$ | $A_3$ | $A_4$ |
|---|---|---|---|---|---|---|---|---|---|---|---|---|---|
| 1.03 | H | H | H | H | H | $CH_3$ | H | H | O | C—H | C—$CH_3$ | C—$CH_3$ | C—H |
| 1.04 | H | H | H | H | H | $CH_3$ | H | H | O | C—H | C—H | C—$CH_3$ | C—$CH_3$ |
| 1.05 | H | H | H | OH | H | $CH_3$ | H | H | O | C—$CH_3$ | C—H | C—H | C—$CH_3$ |
| 1.06 | H | H | H | OH | H | $CH_3$ | H | H | O | C—H | C—H | C—$CH_3$ | C—$CH_3$ |
| 1.07 | H | H | H | H | H | $CH_3$ | H | H | O | C—H | C—H | C—NO2 | C—H |
| 1.08 | H | H | H | H | H | $CH_3$ | H | H | O | C—H | C—H | C—NH2 | C—H |
| 1.09 | H | H | H | H | H | $CH_3$ | H | H | O | C—H | C—$CH_3$ | C—H | C—H |
| 1.10 | H | H | H | H | H | $CH_3$ | H | H | O | C—H | C—H | C—H | C—$CH_3$ |
| 1.11 | H | H | H | H | H | $CH_3$ | H | $CH_3$ | O | C—H | C—H | C—H | C—H |
| 1.12 | H | H | H | H | H | $CH_3$ | H | H | O | C—H | C—I | C—H | C—H |
| 1.13 | H | H | H | H | H | H | H | H | O | C—H | C—H | C—H | C—H |
| 1.14 | H | H | H | H | H | H | $CH_3$ | H | O | C—H | C—H | C—H | C—H |
| 1.15 | H | H | H | H | H | $CH_3$ | H | H | O | C—OH | C—H | C—H | C—$CH_3$ |
| 1.16 | H | H | H | H | H | $CH_3$ | H | H | O | C—H | C—H | C—H | C—OH |
| 1.17 | H | H | H | H | H | $CH_3$ | H | H | O | C—$CH_2OH$ | C—H | C—H | C—H |
| 1.18 | H | H | H | OAc | H | $CH_3$ | H | H | O | C—H | C—H | C—H | C—H |
| 1.19 | H | H | H | OAc | H | $CH_3$ | H | H | O | C—$CH_3$ | C—H | C—H | C—$CH_3$ |
| 1.20 | H | H | H | OAc | H | $CH_3$ | H | H | O | C—H | C—H | C—$CH_3$ | C—$CH_3$ |
| 1.21 | C—$CH_3$ | H | H | H | H | $CH_3$ | H | H | O | C—H | C—H | C—H | C—H |
| 1.22 | C—$CH_3$ | H | H | OH | H | $CH_3$ | H | H | O | C—H | C—H | C—H | C—H |
| 1.23 | C—$CH_3$ | H | H | H | H | $CH_3$ | H | H | O | C—$CH_3$ | C—H | C—H | C—$CH_3$ |
| 1.24 | C—$CH_3$ | H | H | H | H | $CH_3$ | H | H | O | C—H | C—$CH_3$ | C—$CH_3$ | C—H |
| 1.25 | C—$CH_3$ | H | H | H | H | $CH_3$ | H | H | O | C—H | C—H | C—$CH_3$ | C—$CH_3$ |
| 1.26 | C—$CH_3$ | H | H | OH | H | $CH_3$ | H | H | O | C—$CH_3$ | C—H | C—H | C—$CH_3$ |
| 1.27 | C—$CH_3$ | H | H | OH | H | $CH_3$ | H | H | O | C—H | C—H | C—$CH_3$ | C—$CH_3$ |
| 1.28 | C—$CH_3$ | H | H | H | H | $CH_3$ | H | H | O | C—H | C—H | C—NO2 | C—H |
| 1.29 | C—$CH_3$ | H | H | H | H | $CH_3$ | H | H | O | C—H | C—H | C—NH2 | C—H |
| 1.30 | C—$CH_3$ | H | H | H | H | $CH_3$ | H | H | O | C—H | C—$CH_3$ | C—H | C—H |
| 1.31 | C—$CH_3$ | H | H | H | H | $CH_3$ | H | H | O | C—H | C—H | C—H | C—$CH_3$ |
| 1.32 | C—$CH_3$ | H | H | H | H | $CH_3$ | H | $CH_3$ | O | C—H | C—H | C—H | C—H |
| 1.33 | C—$CH_3$ | H | H | H | H | $CH_3$ | H | H | O | C—H | C—I | C—H | C—H |
| 1.34 | C—$CH_3$ | H | H | H | H | H | H | H | O | C—H | C—H | C—H | C—H |
| 1.35 | C—$CH_3$ | H | H | H | H | H | $CH_3$ | H | O | C—H | C—H | C—H | C—H |
| 1.36 | C—$CH_3$ | H | H | H | H | $CH_3$ | H | H | O | C—OH | C—H | C—H | C—$CH_3$ |
| 1.37 | C—$CH_3$ | H | H | H | H | $CH_3$ | H | H | O | C—H | C—H | C—H | C—OH |
| 1.38 | C—$CH_3$ | H | H | H | H | $CH_3$ | H | H | O | C—$CH_2OH$ | C—H | C—H | C—H |
| 1.39 | C—$CH_3$ | H | H | OAc | H | H | $CH_3$ | H | H | O | C—H | C—H | C—H |
| 1.40 | C—$CH_3$ | H | H | OAc | H | H | $CH_3$ | H | H | O | C—$CH_3$ | C—H | C—H |
| 1.41 | C—$CH_3$ | H | H | OAc | H | H | $CH_3$ | H | H | O | C—H | C—H | C—$CH_3$ |

TABLE 2

(II)

| Compound | R1 | R2 | R3 | R4 | R5 | R8 | W | $A_1$ | $A_2$ | $A_3$ | $A_4$ |
|---|---|---|---|---|---|---|---|---|---|---|---|
| 2.00 | H | H | H | H | H | H | O | C—H | C—H | C—H | C—H |
| 2.01 | H | H | H | OH | H | H | O | C—H | C—H | C—H | C—H |
| 2.02 | H | H | H | H | H | H | O | C—$CH_3$ | C—H | C—H | C—$CH_3$ |

TABLE 2-continued

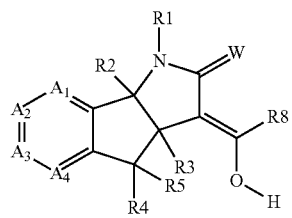

(II)

| Compound | R1 | R2 | R3 | R4 | R5 | R8 | W | $A_1$ | $A_2$ | $A_3$ | $A_4$ |
|---|---|---|---|---|---|---|---|---|---|---|---|
| 2.03 | H | H | H | H | H | H | O | C—H | C—CH$_3$ | C—CH$_3$ | C—H |
| 2.04 | H | H | H | H | H | H | O | C—H | C—H | C—CH$_3$ | C—CH$_3$ |
| 2.05 | H | H | H | OH | H | H | O | C—CH$_3$ | C—H | C—H | C—CH$_3$ |
| 2.06 | H | H | H | OH | H | H | O | C—H | C—H | C—CH$_3$ | C—CH$_3$ |
| 2.07 | H | H | H | H | H | H | O | C—H | C—H | C—NO2 | C—H |
| 2.08 | H | H | H | H | H | H | O | C—H | C—H | C—NH2 | C—H |
| 2.09 | H | H | H | H | H | H | O | C—H | C—CH$_3$ | C—H | C—H |
| 2.10 | H | H | H | H | H | H | O | C—H | C—H | C—H | C—CH$_3$ |
| 2.11 | H | H | H | H | H | CH$_3$ | O | C—H | C—H | C—H | C—H |
| 2.12 | H | H | H | H | H | H | O | C—H | C—I | C—H | C—H |
| 2.13 | H | H | H | H | H | H | O | C—H | C—H | C—H | C—H |
| 2.14 | H | H | H | H | H | H | O | C—H | C—H | C—H | C—H |
| 2.15 | H | H | H | H | H | H | O | C—OH | C—H | C—H | C—CH$_3$ |
| 2.16 | H | H | H | H | H | CH$_3$ | H | H | O | C—CH$_2$OH | C—H |
| 2.17 | H | H | H | H | H | H | O | C—H | C—H | C—H | C—OH |
| 2.18 | H | H | H | OAc | H | CH$_3$ | H | H | O | C—H | C—H |
| 2.19 | H | H | H | OAc | H | CH$_3$ | H | H | O | C—CH$_3$ | C—H |
| 2.20 | H | H | H | OAc | H | CH$_3$ | H | H | O | C—H | C—H |
| 2.21 | C—CH$_3$ | H | H | H | H | H | O | C—H | C—H | C—H | C—H |
| 2.22 | C—CH$_3$ | H | H | OH | H | H | O | C—H | C—H | C—H | C—H |
| 2.23 | C—CH$_3$ | H | H | H | H | H | O | C—CH$_3$ | C—H | C—H | C—CH$_3$ |
| 2.24 | C—CH$_3$ | H | H | H | H | H | O | C—H | C—CH$_3$ | C—CH$_3$ | C—H |
| 2.25 | C—CH$_3$ | H | H | H | H | H | O | C—H | C—H | C—CH$_3$ | C—CH$_3$ |
| 2.26 | C—CH$_3$ | H | H | OH | H | H | O | C—CH$_3$ | C—H | C—H | C—CH$_3$ |
| 2.27 | C—CH$_3$ | H | H | OH | H | H | O | C—H | C—H | C—CH$_3$ | C—CH$_3$ |
| 2.28 | C—CH$_3$ | H | H | H | H | H | O | C—H | C—H | C—NO2 | C—H |
| 2.29 | C—CH$_3$ | H | H | H | H | H | O | C—H | C—H | C—NH2 | C—H |
| 2.30 | C—CH$_3$ | H | H | H | H | H | O | C—H | C—CH$_3$ | C—H | C—H |
| 2.31 | C—CH$_3$ | H | H | H | H | H | O | C—H | C—H | C—H | C—CH$_3$ |
| 2.32 | C—CH$_3$ | H | H | H | H | CH$_3$ | O | C—H | C—H | C—H | C—H |
| 2.33 | C—CH$_3$ | H | H | H | H | H | O | C—H | C—I | C—H | C—H |
| 2.34 | C—CH$_3$ | H | H | H | H | H | O | C—H | C—H | C—H | C—H |
| 2.35 | C—CH$_3$ | H | H | H | H | H | O | C—H | C—H | C—H | C—H |
| 2.36 | C—CH$_3$ | H | H | H | H | H | O | C—OH | C—H | C—H | C—CH$_3$ |
| 2.37 | C—CH$_3$ | H | H | H | H | H | O | C—H | C—H | C—H | C—OH |
| 2.38 | C—CH$_3$ | H | H | H | H | CH$_3$ | H | H | O | C—CH$_2$OH | C—H |
| 2.39 | C—CH$_3$ | H | H | H | OAc | H | CH$_3$ | H | H | O | C—H |
| 2.40 | C—CH$_3$ | H | H | H | OAc | H | CH$_3$ | H | H | O | C—CH$_3$ |
| 2.41 | C—CH$_3$ | H | H | H | OAc | H | CH$_3$ | H | H | O | C—H |

The compounds of Formula (I) according to the invention can be used as plant growth regulators or seed germination promoters by themselves, but they are generally formulated into plant growth regulation or seed germination promotion compositions using formulation adjuvants, such as carriers, solvents and surface-active agents (SFAs). Thus, the present invention further provides a plant growth regulator composition comprising a plant growth regulation compound of Formula (I) and an agriculturally acceptable formulation adjuvant. The present invention further provides a plant growth regulator composition consisting essentially of a plant growth regulation compound of Formula (I) and an agriculturally acceptable formulation adjuvant. The present invention further provides a plant growth regulator composition consisting of a plant growth regulation compound of Formula (I) and an agriculturally acceptable formulation adjuvant. The present invention further provides a seed germination promoter composition comprising a seed germination promoter compound of Formula (I) and an agriculturally acceptable formulation adjuvant. The present invention further provides a seed germination promoter composition consisting essentially of a seed germination promoter compound of Formula (I) and an agriculturally acceptable formulation adjuvant. The present invention further provides a seed germination promoter composition consisting of a seed germination promoter compound of Formula (I) and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by absorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium diisopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The present invention still further provides a method for regulating the growth of plants in a locus, wherein the method comprises application to the locus of a plant growth regulating amount of a composition according to the present invention.

The present invention also provides a method for promoting the germination of seeds, comprising applying to the seeds, or to a locus containing seeds, a seed germination promoting amount of a composition according to the present invention.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The compound of formula (I) or composition of the present invention may be applied to a plant, part of the plant, plant organ, plant propagation material or a surrounding area thereof.

In one embodiment, the invention relates to a method of treating a plant propagation material comprising applying to the plant propagation material a composition of the present invention in an amount effective to promote germination and/or regulate plant growth. The invention also relates to a plant propagation material treated with a compound of formula (I) or a composition of the present invention. Preferably, the plant propagation material is a seed.

The term "plant propagation material" denotes all the generative parts of the plant, such as seeds, which can be used for the multiplication of the latter and vegetative plant materials such as cuttings and tubers. In particular, there may be mentioned the seeds, roots, fruits, tubers, bulbs, and rhizomes.

Methods for applying active ingredients to plant propagation material, especially seeds, are known in the art, and include dressing, coating, pelleting and soaking application methods of the propagation material. The treatment can be applied to the seed at any time between harvest of the seed and sowing of the seed or during the sowing process. The seed may also be primed either before or after the treatment. The compound of formula (I) may optionally be applied in combination with a controlled release coating or technology so that the compound is released over time.

The composition of the present invention may be applied pre-emergence or post-emergence. Suitably, where the composition is being used to regulate the growth of crop plants, it may be applied pre or post-emergence, but preferably post-emergence of the crop. Where the composition is used to promote the germination of seeds, it may be applied pre-emergence.

The rates of application of compounds of Formula I may vary within wide limits and depend on the nature of the soil, the method of application (pre- or post-emergence; seed dressing; application to the seed furrow; no tillage application etc.), the crop plant, the prevailing climatic conditions, and other factors governed by the method of application, the time of application and the target crop. For foliar or drench application, the compounds of Formula I according to the invention are generally applied at a rate of from 1 to 2000 g/ha, especially from 5 to 1000 g/ha. For seed treatment the rate of application is generally between 0.0005 and 150 g per 100 kg of seed.

Plants in which the composition according to the invention can be used include crops such as cereals (for example wheat, barley, rye, oats); beet (for example sugar beet or fodder beet); fruits (for example pomes, stone fruits or soft fruits, such as apples, pears, plums, peaches, almonds, cherries, strawberries, raspberries or blackberries); leguminous plants (for example beans, lentils, peas or soybeans); oil plants (for example rape, mustard, poppy, olives, sunflowers, coconut, castor oil plants, cocoa beans or groundnuts); cucumber plants (for example marrows, cucumbers or melons); fibre plants (for example cotton, flax, hemp or jute); citrus fruit (for example oranges, lemons, grapefruit or mandarins); vegetables (for example spinach, lettuce, asparagus, cabbages, carrots, onions, tomatoes, potatoes, cucurbits or paprika); lauraceae (for example avocados, cinnamon or camphor); maize; rice; tobacco; nuts; coffee; sugar cane; tea; vines; hops; durian; bananas; natural rubber plants; turf or ornamentals (for example flowers, shrubs, broad-leaved trees or evergreens such as conifers). This list does not represent any limitation.

The invention may also be used to regulate the growth, or promote the germination of seeds of non-crop plants, for example to facilitate weed control by synchronizing germination.

Crops are to be understood as also including those crops which have been modified by conventional methods of breeding or by genetic engineering. For example, the invention may be used in conjunction with crops that have been rendered tolerant to herbicides or classes of herbicides (e.g. ALS-, GS-, EPSPS-, PPO-, ACCase- and HPPD-inhibitors). An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. Methods of rending crop plants tolerant to HPPD-inhibitors are known, for example from WO0246387; for example the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Chenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

The compounds of the invention may be made by the following methods.

SCHEME 1-option A

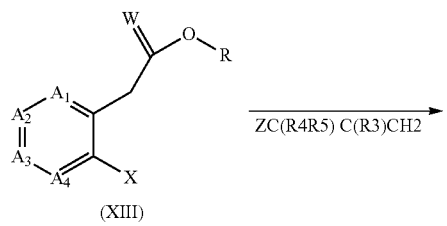

(XIII)

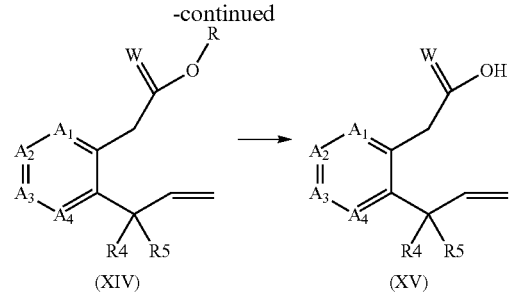

i) Compounds of formula (XIV), wherein R is C1 to C6 alkyl may be made by treatment of compounds of formula (XIII), wherein X is Br or I and R is C1 to C6 alkyl with a allyl derivative of formula ZC(R4R5) C(R3)CH2, wherein Z is a boron or a tin derivatives in the presence of a suitable catalyst/ligand system, often a palladium (0) complex. Compound of formula (XIII), wherein X is Br or I and R is C1 to C6 alkyl known compounds or may be made by methods known to a person skilled in the art.

ii) Compounds of formula (XV) may be made by treatment of compounds of formula (XIV), wherein R is C1 to C6 alkyl by hydrolysis of the ester group with a base such as sodium hydroxide or lithium hydroxide.

SCHEME 1-option B

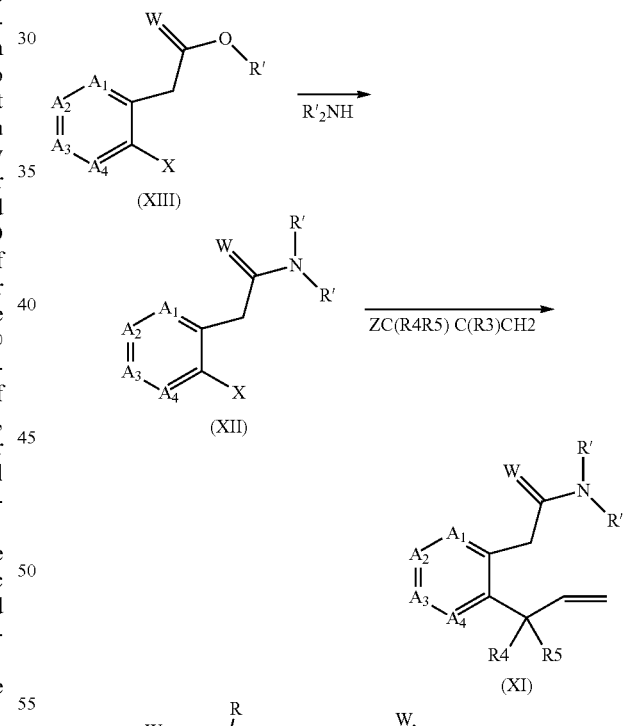

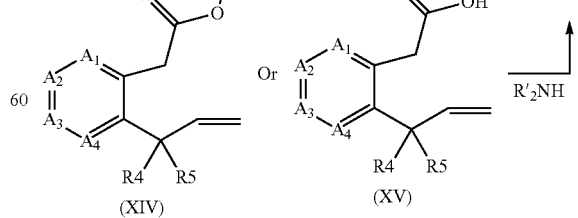

i) Compounds of formula (XII), wherein X is Br or I may be made by treatment of compounds of formula (XIII), wherein R is H, C1-C6alkoxy, Cl, F or Br with an amine of formula HNR'$_2$ wherein R' is not chiral such as isopropyl or R'$_2$ is chiral such as (R,R)-2,5-dimethylpyrrolidine. When R is H such reactions may be carried out in the presence of a coupling reagent, such as DCC (N,N'-dicyclohexyl-carbo-diimide), EDC (1-ethyl-3-[3-dimethyl-amino-propyl] carbodiimide hydrochloride) or BOP—Cl (bis(2-oxo-3-oxazolidinyl)phosphonic chloride), in the presence of a base, such as pyridine, triethylamine, 4-(dimethylamino)pyridine or diisopropylethylamine, and optionally in the presence of a nucleophilic catalyst, such as hydroxybenzotriazole or 1-hydroxy-7-azabenzotriazole. When R is Cl, such reactions may be carried out under basic conditions, for example in the presence of pyridine, triethylamine, 4-(dimethylamino)pyridine or diisopropylethylamine, and optionally in the presence of a nucleophilic catalyst. Alternatively, the reaction may be conducted in a biphasic system comprising an organic solvent, preferably ethyl acetate, and an aqueous solvent, preferably a solution of sodium bicarbonate. When R is C1-C6alkoxy the ester may be converted directly to the amide by heating the ester and amine together in a thermal process. Compounds of formula (XIII) and amines of formula R'$_2$NH are either known compounds or may be made by methods known to a person skilled in the art.

ii) Compounds of formula (XI), wherein R' is not chiral such as isopropyl or R'$_2$ is chiral such as (R,R)-2,5-dimethylpyrrolidine may be made by treatment of compounds of formula (XII), wherein X is Br or I with a allyl derivative of formula ZC(R4R5) C(R3)CH2, Wherein Z is a boron or a tin derivatives in the presence of a suitable catalyst/ligand system, often a palladium (0) complex.

iii) Alternatively, Compounds of formula (XI) may be prepared from a compound of formula (XIV) wherein R is H (compound of formula (XV)), C1-C6alkoxy, Cl, F or Br as described in i).

many other reagents such as Thionyl chloride, Oxaloyl chloride or Phosphorus trichloride. The second reaction is known, to a person skilled in the art by processing via a intramolecular ketene cycloaddition.

SCHEME 2 - option B

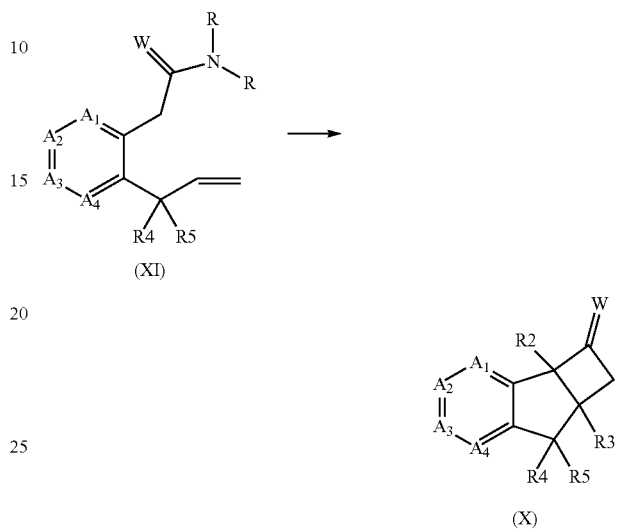

Compounds of formula (X) may be made by treatment of compounds of formula (XI) with a dehydrating agent such as triflic anhydride in presence of a base such as collidine to give a ketene iminium intermediate via intramolecular cycloaddition followed by hydrolysis with water. The use of compounds of formula (XI) wherein R'$_2$ is chiral gives chiral compounds of formula (X), (IX), (VIII), (VII), (VI), (IV), (III), (II), (I).

SCHEME 2 - option A

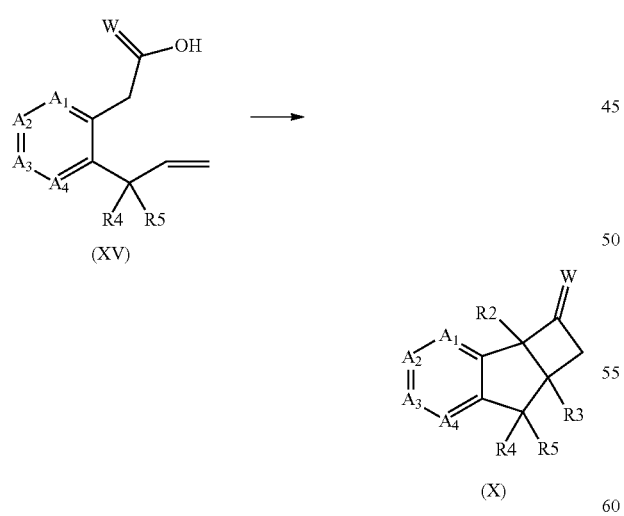

Compounds of formula (X) may be made by treatment of compounds of formula (XV) with a reagent used for the synthesis of acyl chloride such as (1-Chloro-2-methyl-propenyl)-dimethyl-amine, followed by reaction with a base such as triethylamine. The formation of acyl chloride is very well known, to a person skilled in the art and could be done with

SCHEME 3

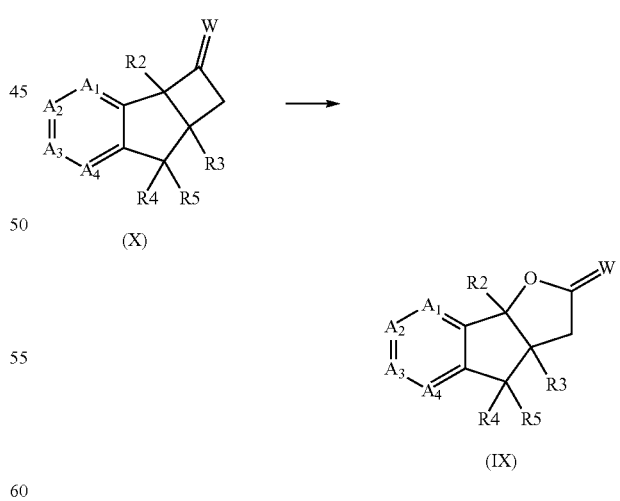

Compounds of formula (IX) may be made by treatment of compounds of formula (X), with a peroxide derivative such as hydrogen peroxide. This reaction is very well known, to a person skilled in the art under the name of Baeyer-Villiger oxidation for the transformation of a carbonyl compounds to lactones or ester.

SCHEME 4

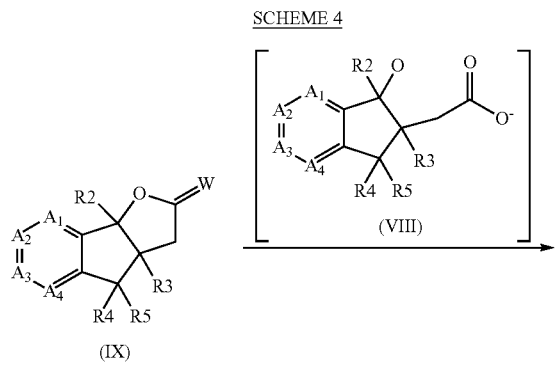

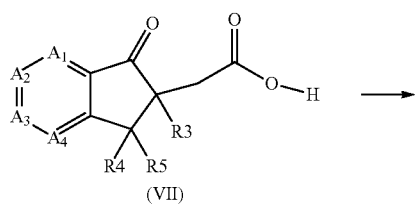

formula (VIII), wherein R2 is hydrogen and W is oxygen by hydrolysis to the acids by treatment with an alkali hydroxide, such as sodium hydroxide, in a solvent, such as water, followed, in situ by oxidation by treatment with an oxidant, such as Ruthenium chloride in presence of Sodium metaperiodate. Compounds of formula (IX) such as 2-Indanacetic acid, 1-hydroxy-γ-lactone are commercially available or prepared as described previously in 4).

ii) Compounds of formula (VI) within R is C1-C6 alkyl and W is oxygen may be prepared from compounds of formula (VII) by esterification by treatment with an alcohol in presence of an acid, such sulphuric acid in methanol or ethanol. Alternatively, compounds of formula (VI) may be prepared from commercial starting material such as indanone derivatives as described in literature (see for example: Bioorganic & Medicinal Chemistry (2008), 16(8), 4438, Journal of the Chemical Society, Perkin Transactions 1: Organic and Bio-Organic Chemistry (1999), (18), 2617, WO2005097093, Monatshefte fuer Chemie (1986), 117(5), 621).

SCHEME 5

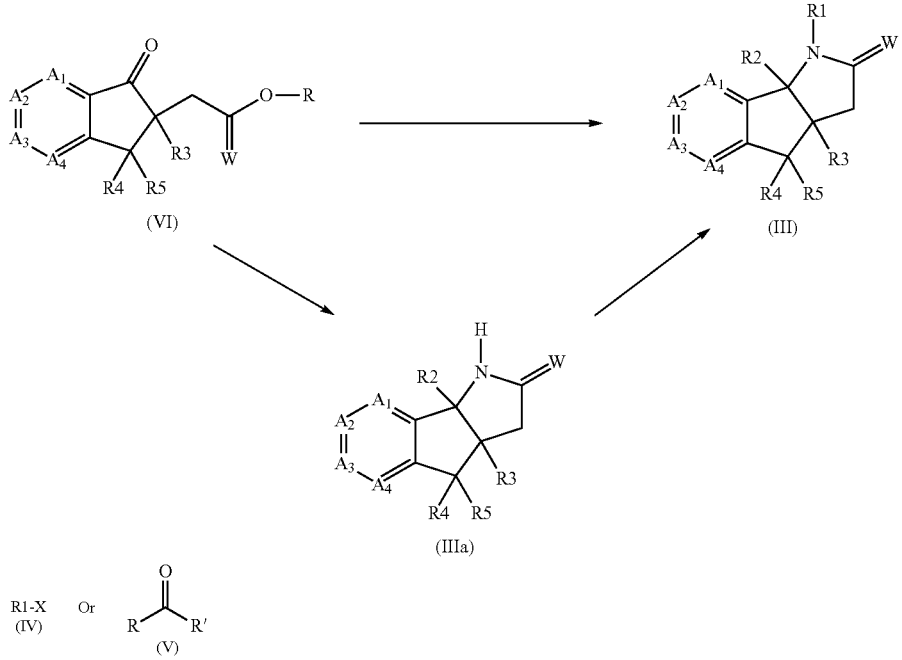

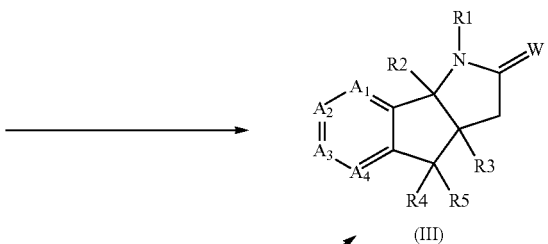

-continued

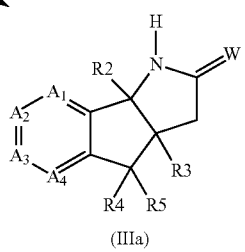

i) Compounds of formula (VII) wherein W is oxygen may be prepared from Compounds of formula (IX) via compound of i) Compounds of formula (III) may be prepared from a compound of formula (VI) wherein R is not a hydrogen such as for example R is a methyl or ethyl via reductive amination by reaction of an substituted amine such as methyl amine and a reducing agent such as sodium cyanoborohydride followed by in situ intramolecular cyclisation.

ii) Alternatively, Compounds of formula (Ma) may be prepared from a compound of formula (VI) wherein R is H via reductive amination by reaction of an amine such as ammonium acetate and a reducing agent such as sodium cyanoborohydride followed by in situ intramolecular cyclisation.

iii) Alternatively, compounds of formula (Ma) can be prepared from a compound of formula (VI) via formation of the oxime using a hydroxylamine salt and a base such as sodium acetate or pyridine, followed by reduction of the intermediate oxime using hydrogenation with $H_2$ and a catalyst such as Pd/C or Raney Nickel, or other known methods such as zinc in acetic acid.

Compounds of formula (III), wherein R1 is not hydrogen, may be prepared from a compound of formula (Ma) (wherein R1 is H) via alkylation by reaction of the amide with an alkylating agent such as an alkyl halide in the presence of a base such as sodium hydride.

Compounds of formula (III), wherein R1 is an aromatic or heteroaromatic group, may be prepared from a compound of formula (Ma) (wherein R1 is H) by reaction of the amide with an aromatic or heteroaromatic compound of formula ArX, X being an halogen, in the presence of a base such as potassium phosphate and a suitable catalyst, often a copper (I) salt and a ligand such as dimethylethane-1,2-diamine.

Compounds of formula (III), wherein R1 is a carbonyl derivative, may be prepared by acylation of a compound of formula (Ma) with a compound of formula (V), wherein R is OH, in the presence of a coupling reagent, such as DCC (N,N'-dicyclohexylcarbodiimide), EDC (1-ethyl-3-[3-dimethylamino-propyl]carbodiimide hydrochloride) or BOP—Cl (bis(2-oxo-3-oxazolidinyl)phosphonic chloride), in the presence of a base, such as pyridine, triethylamine, 4-(dimethylamino)pyridine or diisopropylethylamine, and optionally in the presence of a nucleophilic catalyst, such as hydroxybenzotriazole. Optionally, when R is Cl or OC(O)C1-C6alkoxy, the acylation reaction may be carried out under basic conditions (for example in the presence of pyridine, triethylamine, 4-(dimethylamino)pyridine or diisopropylethylamine), optionally in the presence of a nucleophilic catalyst. Alternatively, the reaction may be conducted in a biphasic system comprising an organic solvent, preferably ethyl acetate, and an aqueous solvent, preferably a solution of sodium bicarbonate. Optionally, when R is $C_1$-$C_6$alkoxy, the amide may be prepared by heating the ester (V) and amide (Ma) together. R' may be alkyl or alkoxy group. In addition, Compounds of formula (III) may be prepared, under racemic form as described in Journal of Pharmaceutical Sciences 1973 Vol. 62, No. 8, p 1363, Journal of Organic Chemistry (1994), 59(2), 284, Russian Journal of Organic Chemistry, Vol. 41, No. 3, 2005, pp. 361 or WO84/00962.

Compounds of formula (III) wherein $A_1, A_2, A_3$ and $A_4$ are independently C—CN can be prepared from compounds of formula (III) wherein $A_1, A_2, A_3$ and $A_4$ are independently C—X (X being an halogen) using a palladium catalyst such as palladium triphenylphosphine tetrakis and a cyanide salt such as zinc cyanide.

Compounds of formula (III) wherein $A_1, A_2, A_3$ and $A_4$ are independently C—$NO_2$ can be prepared from compounds of formula (III) wherein $A_1, A_2, A_3$ and $A_4$ are independently C—H by nitration using for example nitric acid in the presence of sulphuric acid.

Compounds of formula (III) wherein $A_1, A_2, A_3$ and $A_4$ are independently a C-allyl or a C-allyl substituted can be prepared by the reaction of compounds of formula (III) wherein $A_1, A_2, A_3$ and $A_4$ are independently C—X (X being a leaving group, such as halogen) with an allyl boron or an allyl tin derivative in the presence of a suitable catalyst/ligand system, often a palladium (0) complex. These reactions are known to the person skilled in the art as Stille coupling and Suzuki coupling respectively, see for example: Strategic Applications of Named Reactions in Organic Synthesis Kurti, Laszlo; Czako, Barbara; Editors. USA. (2005), Publisher: Elsevier Academic Press, Burlington, Mass. Page 448 (Suzuki coupling) and p 438 (Stille coupling) and cited references.

Compounds of formula (III) wherein $A_1, A_2, A_3$ and $A_4$ are as described for the compound of formula (I) can be prepared by hydrogenation of the compound of formula (III) wherein $A_1, A_2, A_3$ and $A_4$ are independently a C-allyl derivative using a standard hydrogenation catalyst such as palladium on charcoal.

Compounds of formula (III), wherein R4 or R5 are not hydrogen, may be prepared from a compound of formula (Ma) (wherein R4 and R5 are H) via benzylic oxidation using an oxidant such as potassium permanganate or chromium oxide to give the ketone (R4=R5=O). Compound (III), wherein R4=OH and R5=H can be prepared from the corresponding ketone by reduction of the ketone with a reducing agent such as sodium borohydride. Alternatively, the compound or formula (III) wherein R4=OAc and R5=H can be prepared directly by oxidation with (diacetoxyiodo)benzene in the presence of p-toluenesulfonamide and iodine. Compound (III), wherein R4=F and R5=H can be prepared from the compound (III), wherein R4=OH and R5=H by reaction with a fluorinating agent such as diethylaminosulfur trifluoride or Deoxo-Fluor™.

SCHEME 6

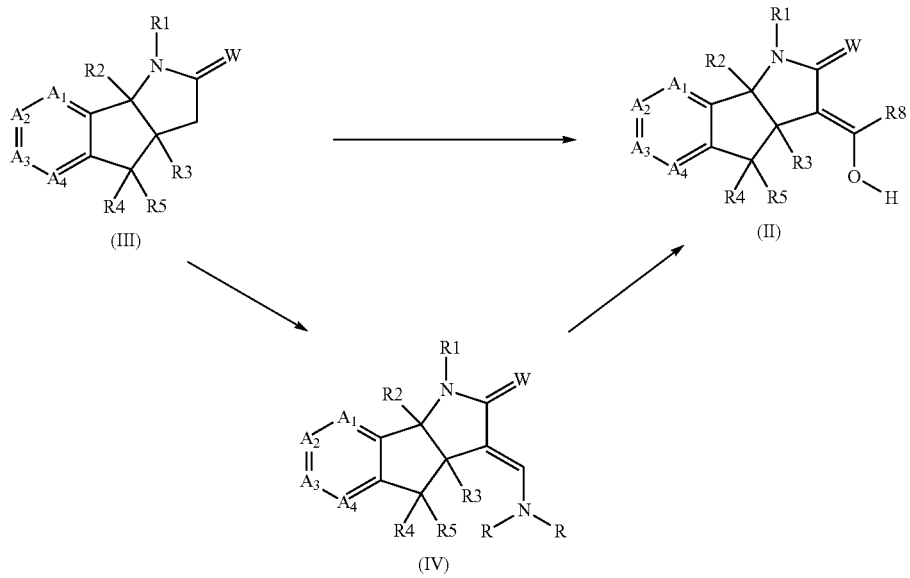

Compounds of formula (II) may be prepared from a compound of formula (III) via reaction with a formic ester derivative such as the methyl formate in presence of a base such as lithium diisopropylamide or potassium tert-butylate. Alternatively, compounds of formula (II) may be prepared from a compound of formula (IV) via hydrolysis with an acid such as hydrogen chloride. Compounds of formula (IV) may be prepared from a compounds of formula (III) via reaction with a Bredereck's reagent (t-Butoxybis(dimethylamino)methane) wherein R is methyl or analogue.

Compounds of formula (II) wherein $A_1$, $A_2$, $A_3$ and $A_4$ are as described for the compound of formula (I) can be prepared by hydrogenation of the compound of formula (II) where wherein $A_1$, $A_2$, $A_3$ and $A_4$ are independently a C-allyl derivative using a standard hydrogenation catalyst such as palladium on charcoal.

Compounds of formula (II) wherein R1 is a carbonyl can be prepared from compound of formula (II) wherein R1 is H by acylation followed by selective hydrolysis of the diacylated product. The acylation can be carried out by reaction of the compound (II) with a compound of formula R1X where X is halogen or OH or $(R1)_2O$ under basic conditions (for example in the presence of pyridine, triethylamine, 4-(dimethylamino)pyridine or diisopropylethylamine), optionally in the presence of a nucleophilic catalyst such as 4-(dimethylamino)pyridine. The hydrolysis can be carried out in an alcoholic solvent in the presence of a base such as potassium carbonate.

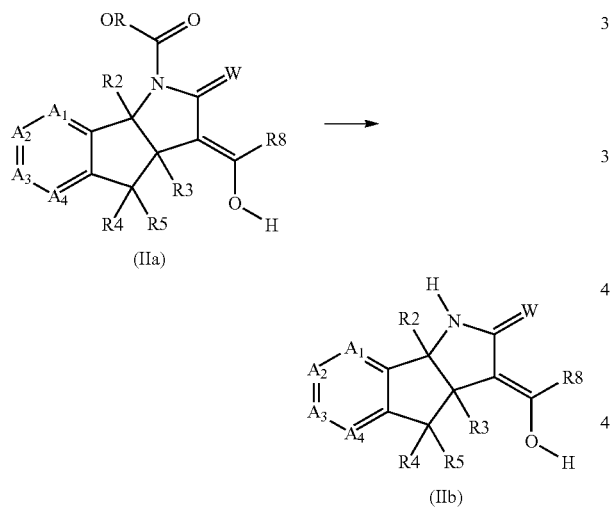

(IIa)

(IIb)

Compounds of formula (IIb) can be prepared from a compound of formula (IIa) wherein R is an alkyl group such as tert butyl via treatment with an acid such as trifluoroacetic acid or HCl.

SCHEME 7

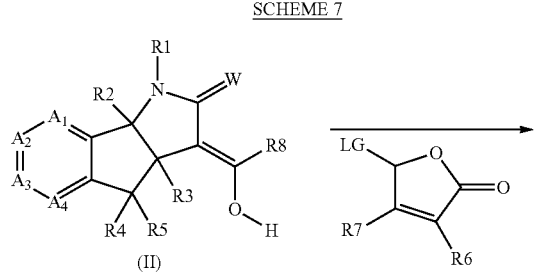

(II)

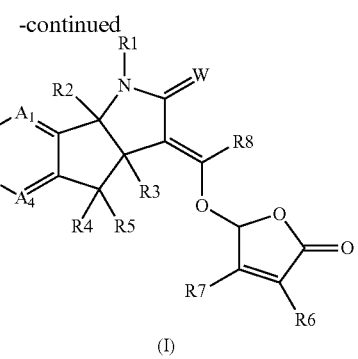

(I)

Compounds of formula (I) may be prepared from a compounds of formula (II) via nucleophilic substitution of a 5H-furanone derivative having a leaving group (LG) and LG is a leaving group, such as bromine in position 5 in presence of a base such as for example potassium tert-butylate or Hunig's base.

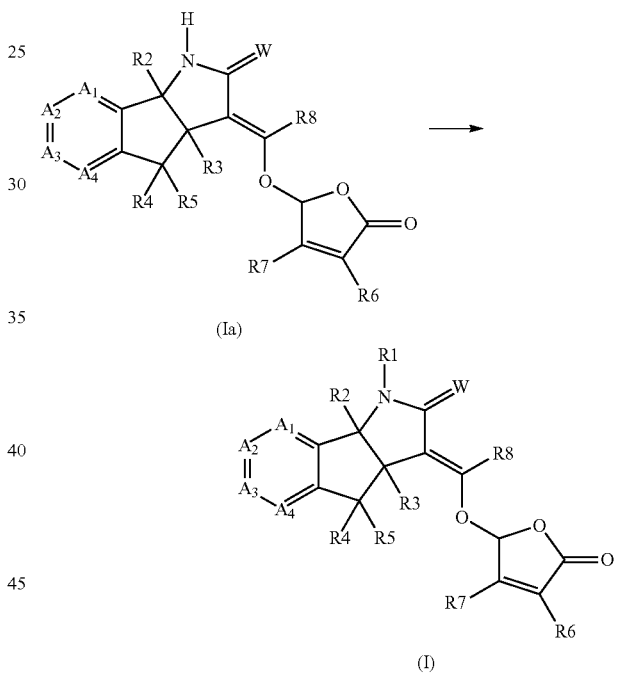

(Ia)

(I)

Alternatively, Compounds of formula (I), wherein $R^1$ is alkyl derivatives or benzyl derivatives, may be prepared from a compound of formula (Ia) wherein $R^1$ is H via alkylation by reaction of the amine with an alkylating agent such as an alkyl halide, benzyl halide optionally in the presence of a base such as sodium hydride.

Alternatively, Compounds of formula (I), wherein a carbonyl derivative, may be prepared from a compound of formula (Ia) wherein $R^1$ is H via acylation with a compound of formula (V), wherein R is OH, in the presence of a coupling reagent, such as DCC(N,N'-dicyclohexylcarbodiimide), EDC (1-ethyl-3-[3-dimethylamino-propyl]carbodiimide hydrochloride) or BOP—Cl (bis(2-oxo-3-oxazolidinyl)phosphonic chloride), in the presence of a base, such as pyridine, triethylamine, 4-(dimethylamino)pyridine or diisopropylethylamine, and optionally in the presence of a nucleophilic catalyst, such as hydroxybenzotriazole. Optionally, when R is Cl or OC(O)C1-C6alkoxy, the acylation reaction may be carried out under basic conditions (for example in the presence of pyridine, triethylamine, 4-(dimethylamino)pyridine or diisopropylethylamine), optionally in the presence of a nucleophilic catalyst. Alternatively, the reaction may be conducted in a biphasic system comprising an organic solvent, preferably ethyl acetate, and an aqueous solvent, preferably a solution of sodium bicarbonate. Optionally, when R is $C_1$-$C_6$alkoxy, the amide may be prepared by heating the ester (V) and amide (Ia) together. R' may be alkyl or alkoxy group.

Compounds of formula (I), wherein W is sulfur, may be prepared from a compound of formula (I), wherein W is oxygen, by treatment with a thio-transfer reagent, such as Lawesson's reagent or phosphorus pentasulfide.

EXAMPLES

The following HPLC-MS methods were used for the analysis of the compounds:

Method A: Spectra were recorded on a ZQ (Waters Corp. Milford, Mass., USA) mass spectrometer equipped with an electrospray source (ESI; source temperature 100° C.; desolvation temperature 250° C.; cone voltage 30 V; cone gas flow 50 L/Hr, desolvation gas flow 400 L/Hr, mass range: 100 to 900 Da) and an Agilent 1100 LC (column: Gemini C18, 3 um particle size, 110 Angström, 30×3 mm (Phenomenex, Torrance, Calif., USA); column temperature: 60° C.; flow rate 1.7 mL/min; eluent A: $H_2O$/HCOOH 100:0.05; eluent B: MeCN/MeOH/$HCO_2H$ 80:20:0.04; gradient: 0 min 5% B; 2-2.8 min 100% B; 2.9-3 min 5% B; UV-detection: 200-500 nm, resolution 2 nm. The flow was split postcolumn prior to MS analysis.

Method B: Spectra were recorded on a ZMD (Micromass, Manchester UK) mass spectrometer equipped with an electrospray source (ESI; source temperature 80° C.; desolvation temperature 200° C.; cone voltage 30 V; desolvation gas flow 600 L/Hr, mass range: 100 to 900 Da) and an Agilent 1100 LC (column: Gemini C18, 3 um particle size, 110 Angström, 30×3 mm (Phenomenex, Torrance, Calif., USA); column temperature: 60° C.; flow rate 1.7 mL/min; eluent A: $H_2O$/$HCO_2H$ 100:0.05; eluent B: MeCN/MeOH/$HCO_2H$ 80:20: 0.04; gradient: 0 min 5% B; 2-2.8 min 100% B; 2.9-3 min 5% B; UV-detection: 200-500 nm, resolution 2 nm. The flow was split postcolumn prior to MS analysis.

Method C: Spectra were recorded on an API2000/Q-TRAP (Applied Biosystems). mass spectrometer equipped with an electrospray source (ESI; source temperature 200° C.; capillary 5.5 Kv, (Declustering Potential 50V). (Focusing Potential 400V, Entrance Potential 10V), (Curtain Gas 30PS1, GS1 40PS1, GS2 50PSI), mass range: 100 to 800 Da) and a Shimadzu SIL HTC/UFLC (column: see table H); column temperature: 25° C.; flow rate 1.2 mL/min; eluent A: 10 mM $NH_4OAc$ in $H_2O$; eluent B: MeCN; gradient: 0.01 min 10% B; 1.5 min 30% B; 3-4 min 90% B; 5 min 10% B; UV-detection: 220 and 260 nm, The flow was split post column prior to MS analysis.

Method D: Spectra were recorded on a Agilent G1956A mass spectrometer equipped with an electrospray source (ESI; source temperature 100° C.; desolvation temperature 350° C.; capillary 4 kV; desolvation gas flow 10 L/Hr, mass range: 100 to 1000 Da) and an Agilent 1100 LC (column: Discovery HS-C18, 3 um particle size, 110 Angström, 50×4.6 mm, Supelco 569250-U); column temperature: n.a.; flow rate 2.20 mL/min; eluent A: MeCN/TFA 100:0.05; eluent B: $H_2O$/TFA 100:0.05; gradient: 0 min 10% A, 5 min 90% A, 6 min 99% A; UV-detection: 190-400 nm, resolution 2 nm.

Method E: Spectra were recorded on a SQD Mass Spectrometer (Waters Corp. Milford, Mass., USA) mass spectrometer equipped with an electrospray source (ESI; source temperature 150° C.; desolvation temperature 250° C.; cone voltage 45 V; desolvation gas flow 650 L/Hr, mass range: 100 to 900 Da) and an Agilent UP LC (column: Gemini C18, 3 um, 30×2 mm (Phenomenex, Torrance, Calif., USA); LC (column: Gemini C18, 3 um particle size, 110 Angström, 30×3 mm (Phenomenex, Torrance, Calif., USA); column temperature: 60° C.; flow rate 0.85 mL/min; eluent A: $H_2O$/MeOH/$HCO_2H$ 100:5:0.05; eluent B: MeCN/HCOOH 100:0.05; gradient: 0 min 0% B; 0-1.2 min 100% B; 1.2-1.50 min 100% B; UV-detection: 210-500 nm, resolution 2 nm. The flow was split postcolumn prior to MS analysis.

The following abbreviations are used throughout this section: s=singlet; bs=broad singlet; d=doublet; dd=double doublet; dt=double triplet; t=triplet, tt=triple triplet, q=quartet, m=multiplet; Me=methyl; Et=ethyl; Pr=propyl; Bu=butyl; M.p.=melting point; RT=retention time, $MH^+$=molecular cation (i.e. measured molecular weight).

Example I1

(N,N)-Diisopropyl 2-allylphenylacetamide

Step 1: (N,N)-Diisopropyl 2-iodophenylacetamide

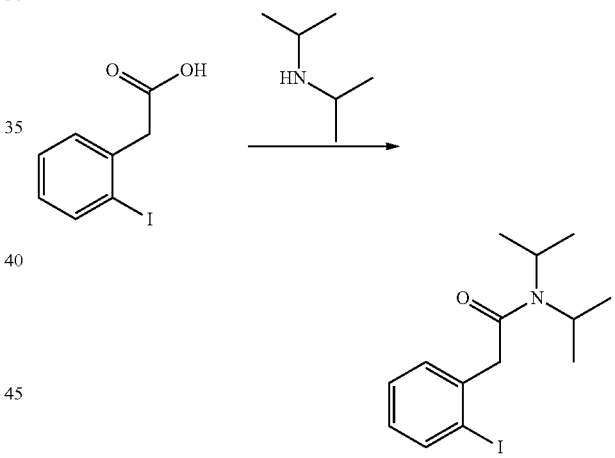

To a solution of 2-iodophenylacetic acid (11.0 g, 42.0 mmol, commercially available) in dichloromethane (85 mL) was added oxalyl chloride (7.11 mL, 84 mmol) followed by 2 drops of dimethyl formamide. The solution as stirred at room temperature for 2 h and the solvents were removed in vacuo. The residue was taken up in dichloromethane (100 mL) and cooled at 0° C. Diisopropylamine (17.6 mL, 126 mmol) was then added and the solution as warmed to room temperature. The solvents were removed in vacuum. The residue was partitioned between ethyl acetate and water and extracted with ethyl acetate. The combined organic layers were washed with hydrogen chloride (1N), brine, dried and concentrated to give 14.3 g of (N,N)-Diisopropyl 2-iodophenylacetamide (White solid, 99%). $C_{14}H_{20}INO$, MW: 345.23; LCMS (method A) RT 1.90 min; Mass 346 (100%, $MH^+$), 268 (10%, $MNa^+$); IR: 2965, 1634, 1438, 1369, 1337 $cm^{-1}$; $^1H$ NMR (400 MHz, $CDCl_3$) δ 7.84 (d, 1H), 7.22-7.35 (m, 3H), 6.84-6.97 (m, 1H), 3.91 (m, 1H), 3.76 (s, 2H), 3.43 (m, 1H), 1.46 (d, 3H), 1.15 (d, 6H) ppm.

Step 2: (N,N)-Diisopropyl 2-allylphenylacetamide

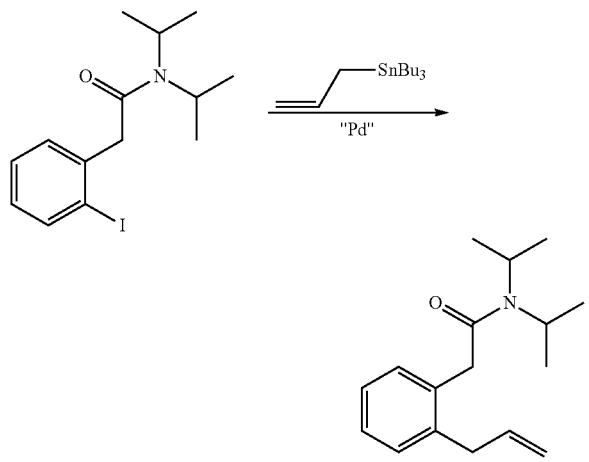

To a degazed solution of the (N,N)-Diisopropyl 2-iodophenylacetamide (Step 1, 0.235 g, 0.681 mmol) in toluene (17 mL) was added Tetrakis(triphenylphosphine)palladium (84 mg, 0.072 mmol). The resulting solution was heated to 110° C. for 20 h and then cooled down. The solvents were removed in vacuo and the yellow oil was partitioned between acetonitrile (30 mL) and hexane (30 mL) and the acetonitrile layer was washed with hexane (2*30 mL). The acetonitrile was removed in vacuo and the residue was purified by flash chromatography eluting with cyclohexane and ethyl acetate (9/1 the 4/1) to give (N,N)-Diisopropyl 2-allylphenylacetamide (Colourless oil, 250 mg, 67%). $C_{17}H_{25}NO$; MW: 259.39; LCMS (method A) RT 1.97 min; ES: 260 (100%, MH+); IR. 2965, 1634, 1466, 1439, 1369, 1335 cm$^{-1}$; $^1$H NMR (400 MHz, CDCl$_3$) δ 7.09-7.23 (4H, m), 5.95 (1H, m), 5.07 (1H, dd), 4.99 (1H, dd), 3.85 (1H, m), 3.66 (2H, s), 3.38-3.50 (1H, m), 3.36 (2H, d), 1.45 (7H, d), 1.08 (6H, d) ppm.

Alternative to Step 2

To a degazed solution of the (N,N)-Diisopropyl 2-iodophenylacetamide (Step 1, 0.50 g, 1.44 mmol) in tetrahydrofurane (10 mL) was added Tetrakis(triphenylphosphine)palladium (39 mg, 0.034 mmol), caesium fluoride (0.207 mg, 1.40 mmol) and pinacol allylboronate (0.229 mg, 1.361 mmol). The resulting solution was heated to reflux for 4 h and water was added (20 mL). The aqueous layer was extracted with diethyl ether and the combined organic layers were washed with brine, dried and concentrated. The residue was purified by flash chromatography eluting with cyclohexane and ethyl acetate (9/1 the 4/1) to give (N,N)-Diisopropyl 2-allylphenylacetamide (Colourless oil, 135 mg, 76%). The anatical data were identical to the previous coupling procedure.

Example I2

2-(2-Allyl-phenyl)-1-((2R,5R)-2,5-dimethyl-pyrrolidin-1-yl)-ethanone

Step 1: Methyl 2-allylphenylacetate

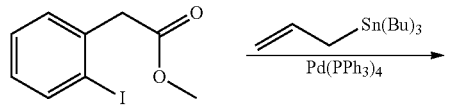

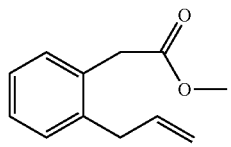

To a solution of methyl 2-iodophenylacetate (1.00 g, 3.62 mmol, prepared from the corresponding acid according to litt. Tetrahedron 63, 2007, 9979) in toluene (45 mL) was added Tetrakis(triphenylphosphine)palladium (209 mg, 0.0.181 mmol) and allyl tributylstannane (1.35 mL, 4.34 mmol). The resulting solution was heated to 110° C. for 20 h and then cooled down. The solvents were removed in vacuo. The yellow oil was partitioned between acetonitrile (30 mL) and hexane (30 mL) and the acetonitrile layer was washed with hexane (2*30 mL). The acetonitrile was removed in vacuo and the residue was purified by flash chromatography eluting with cyclohexane and ethyl acetate (15/1) to give Methyl 2-allylphenylacetate (colourless oil, 446 mg, 65%). $C_{12}H_{14}O_2$; MW: 190.24; LCMS (method A) RT 1.74 min; ES: 191 (100%, MH+); IR. 2951, 1734 cm$^{-1}$; $^1$H NMR (400 MHz, CDCl$_3$) δ 7.14-7.41 (4H, m), 5.99 (1H, m), 5.12 (1H, m), 5.03 (1H, m), 3.73 (3H, s), 3.72 (2H, s), 3.47 (2H, dt) ppm.

Step 2: 2-Allyl phenyl acetic acid

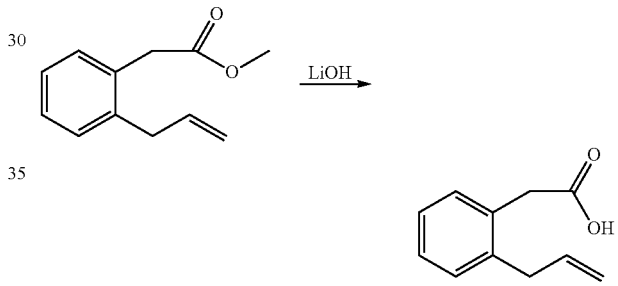

To a solution of the Methyl 2-allylphenylacetate (Step 1, 0.400 mg. 2.10 mmol) in tetrahydrofurane (10 mL) was added Lithium hydroxide (0.097 g, 2.31 mmol) in water (10 mL). The solution was stirred at room temperature for 3 h and was concentrated in vacuo. Water (40 mL) was added and the pH was adjusted to 1. The solution was extracted with dichloromethane and the combined organic layers were dried and concentrated to give 2-allyl phenyl acetic acid (yellow oil, 363 mg, 98%); $C_{11}H_{12}O_2$; MW: 176.22; ES– 175; IR 1702 cm$^{-1}$; $^1$H NMR (400 MHz, CDCl$_3$) δ 7.16-7.38 (4H, m), 5.99 (1H, m), 5.11 (1H, m), 5.04 (1H, m), 3.73 (2H, s), 3.47 (2H, dt) ppm.

Example I3

2-(2-Allyl-phenyl)-1-((2R,5R)-2,5-dimethyl-pyrrolidin-1-yl)-ethanone

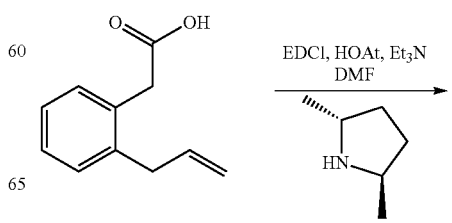

-continued

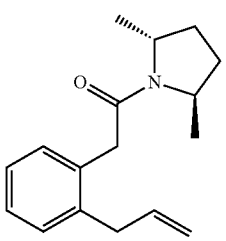

To a solution of 2-allyl phenyl acetic acid (0.050 mg, 0.284 mmol) in Dimethylformamide (5 mL) was added 3-[3-(Dimethylamino)propyl]-1-ethylcarbodiimide hydrochloride (EDCI, 0.075 mmol, 0.397 mmol), 1-Hydroxy-7-azabenzotriazole (HOAt, 0.054 mg, 0.397 mmol), (2R,5R)-dimethylpyrrolidine (0.034 mL, 0.298 mmol) followed by triethylamine (0.118 mL, 0.851 mmol). The solution was stirred for 18 h and water was added (20 mL). The aqueous layer was extracted with diethylether and the combined organic layers were washed with brine, dried and concentrated. The residue was purified by flash chromatography eluting with cyclohexane and ethyl acetate (9/1 the 4/1) to give 2-(2-allyl-phenyl)-1-((2R,5R)-2,5-dimethyl-pyrrolidin-1-yl)-ethanone (colourless oil, 73 mg, 99%). $C_{17}H_{23}NO$; MW: 257.38; LCMS (method A) RT 1.84 min; ES 258 (100%, MH$^+$), 280 (10%, MNa$^+$); $^1$H NMR (400 MHz, CDCl$_3$) δ 7.08-7.24 (4H, m), 5.97 (1H, m), 5.07 (1H, m), 4.99 (1H, m), 4.29 (1H, q), 4.01 (1H, q), 3.76 (1H, d), 3.58 (1H, d), 3.39 (2H, m), 2.08-2.26 (2H, m), 1.52-1.63 (2H, m), 1.23 (3H, d), 1.21 (3H, d) ppm.

Example I4

1,2a,7,7a-tetrahydro-2H-Cyclobut[a]inden-2-one

Method A (Via the Formation of Keteiminium)

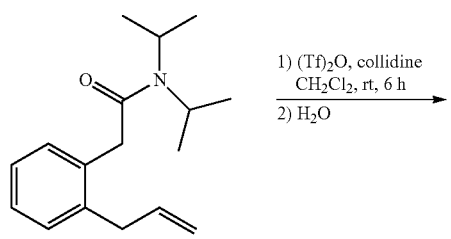

To a solution of (N,N)-diisopropyl 2-allylphenylacetamide (Example I1, 0.100 g, 0.386 mmol) in dichloromethane (10 mL) was added collidine (0.061 mL, 0.463 mmol) followed by triflic anhydride (0.072 mL, 0.424 mmol). The solution was stirred at room temperature for 24 h. The solvents were removed in vacuo and the residue was taken up in carbon tetrachloride (4 mL) and water (4 mL) and the biphasic mixture was stirred at 70° C. for 6 h. The aqueous layer was extracted with dichloromethane and the combined organic layers were dried and concentrated. The residue was purified by flash chromatography eluting with cyclohexane and ethyl acetate (20/1) to give 1,2a,7,7a-tetrahydro-2H-Cyclobut[a]inden-2-one (colourless oil, 48 mg, 74%); MW: 158.22; LCMS (method A) RT 1.51 min; ES: 159 (20%, MH$^+$), 143 (100%); IR: 2921 1777 cm$^{-1}$; $^1$H NMR (400 MHz, CDCl$_3$) δ 7.29-7.36 (2H, m), 7.23-7.29 (2H, m), 4.65-4.80 (1H, m), 3.46 (1H, dd), 3.36 (1H), 3.11-3.19 (1H, m) 3.08 (1H, d), 2.88 (1H, m) ppm.

*Method B (Via the Formation of a Ketene):

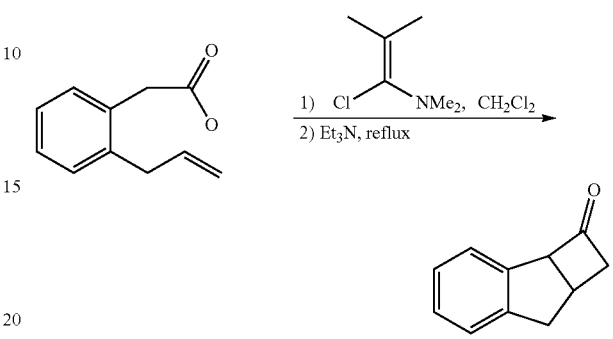

To a solution of 2-allyl phenyl acetic acid (Example I2, Step 2, 0.095 g, 0.539 mmol) in dichloromethane (25 mL) was added at 0° C. 1-chloro-N,N,2-trimethyl-1-propenylamine (0.078 mL, 0.593 mmol). The solution was stirred for 1 h and then heated to reflux. Then, a solution of triethylamine (0.082 mL, 0.593 mmol) in dichloromethane (4 mL) was added slowly over two hours to the solution of the acid chloride at reflux. The reaction mixture was stirred for another 2 h and then cooled down. The solvents were removed in vacuo and the residue was purified by flash chromatography eluting with cyclohexane and ethyl acetate (20/1) to give 1,2a,7,7a-tetrahydro-2H-Cyclobut[a]inden-2-one (colourless oil, 56 mg, 66%) The analytical data were identical to the product obtained with the method A.

Example I5

Tetrahydroindeno[1,2-b]furan-2-one derivative

Example 1 rac-Tetrahydroindeno[1,2-b]furan-2-one

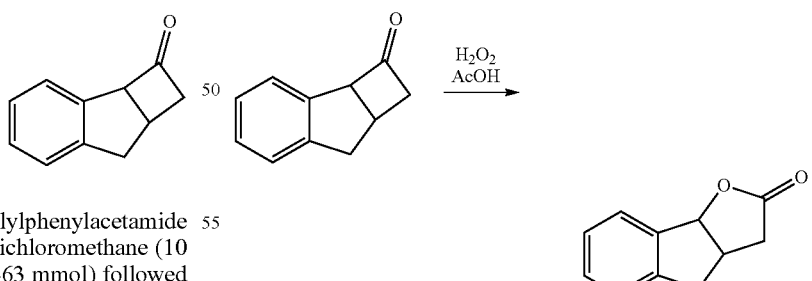

A solution of 1,2a,7,7a-tetrahydro-2H-Cyclobut[a]inden-2-one (Example I4, 0.377 mg, 2.383 mmol) in acetic acid (5 mL) and water (0.5 mL) was cooled at 0° C. and hydrogen peroxide (30% in water, 0.810 mL, 7.14 mmol) was added. The solution as stirred for 3 h at 0° C. and the reaction mixture was poured into saturated solution of sodium hydrogenocarbonate. The solution was extracted with ethyl acetate and the combined organic layers were washed with brine, dried and concentrated. The residue was purified by flash chromatography eluting with cyclohexane and ethyl acetate (4/1) to give rac-Tetrahydroindeno[1,2-b]furan-2-one (Colourless oil, 383 mg, 92%), that solidified upon cooling (data match with litt data, CAS 4471-33-4). $C_{11}H_{10}O_2$; MW: 174.20; LCMS (method A) RT 1.32 min; ES: 175 (60%, MH$^+$), 129 (100%); IR: 1769 cm$^{-1}$; $^1$H NMR (400 MHz, CDCl$_3$) δ 7.50 (1H, d), 7.25-7.39 (4H, m), 5.91 (1H, d), 3.28-3.45 (2H, m), 2.86-2.97 (2H, m), 2.41 (1H, dd) ppm.

Example 2

3a(R),8b(S)tetrahydroindeno[1,2-b]furan-2-one

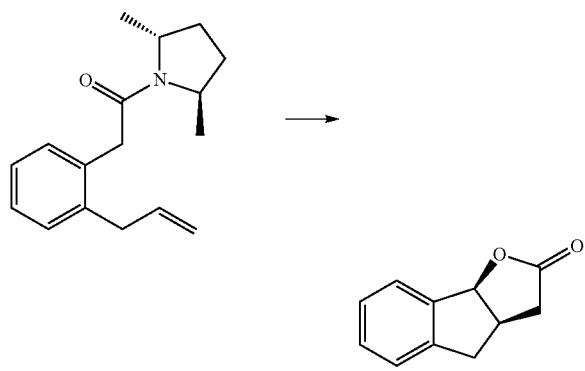

The chiral lactone was obtained from the 2-(2-Allyl-phenyl)-1-((2R,5R)-2,5-dimethyl-pyrrolidin-1-yl)-ethanone (Example I3) using method A (Example I4) for the cyclobutanone formation and Baeyer Villiger oxidation as described above. The enantiomeric excess was determined by chiral HPLC analysis using a CHIRALPAK® IC column (Cellulose tris (3,5-dichlorophenylcarbamate) immobilized on 5 μm silica-gel, 0.46 cm×25 cm, DAD Wavelength (nm): 270); solvent gradient: Heptan/2-Propanol/0.1% DEA 97/03/0.1; flow rate 1 mL/min; retention time enantiomer 1: 32 min (96%), enantiomer 2: 38 min (4%); ee=92%; [□]$_D$=−107° (litt: *J. Agric. Food Chem.* 1997, 2278-2283)

Example I6

(1-Oxo-indan-2-yl)-acetic acid methyl ester derivatives

Example I6(a)

(1-Oxo-indan-2-yl)-acetic acid methyl ester (H1)

Step 1: (1-Oxo-indan-2-yl)-acetic acid

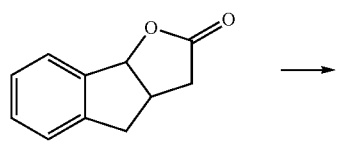

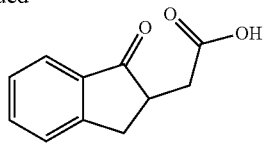

To a suspension of Tetrahydroindeno[1,2-b]furan-2-one (Example I5 or commercially available, 0.200 g, 1.15 mmol) in water (20 mL) was added sodium hydroxide (0.051 g, 1.26 mmol) and the solution was heated to 100° C. for one hour. The solution was cooled down to rt and Ruthenium(III) chloride hydrate (0.048 g, 0.230 mmol) was added followed by sodium periodate (0.368 mg, 1.72 mmol) in water (5 mL) dropwise. The solution was stirred at rt for 1 h and isopropanol was added (0.2 mL). The pH was acidified to 1 using 2M HCl and the reaction was filtered. The filtrate was extracted with dichloromethane (3*30 mL) and the combined organic layers were washed with water (30 mL), dried and concentrated to give (1-Oxo-indan-2-yl)-acetic acid (Pale yellow solid, 170 mg, 78%). $C_{11}H_{10}O_3$; MW: 190.2. LCMS (method A) RT 1.16 min; ES− 189 (35%, MH$^+$), 175 (70%), 145 (100%), 127 (90%). $^1$H NMR (400 MHz, CD$_3$OD) δ 7.71 (1H, d), 7.65 (1H, t), 7.54 (1H, d), 7.41 (1H, t), 3.39-3.51 (1H, m), 2.83-3.02 (3H, m), 2.70 (1H, m) ppm.

Step 2: (1-Oxo-indan-2-yl)-acetic acid methyl ester (H1)

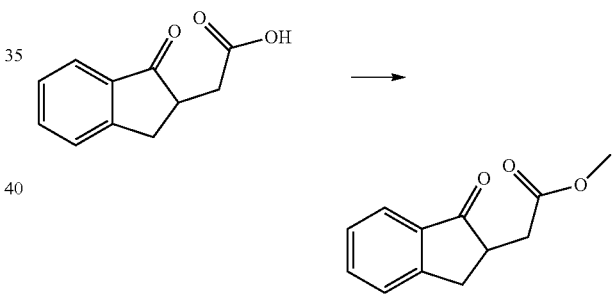

To a solution of (1-Oxo-indan-2-yl)-acetic acid (Step 1, 2.00 g) in methanol (10 mL) at 0° C. was added sulphuric acid (2 mL). The solution was stirred for 2 h and then diluted with water (50 mL) and extracted with ethyl acetate. The combined organic layers were washed with sat. sodium hydrogenocarbonate, dried and concentrated to give (1-Oxo-indan-2-yl)-acetic acid methyl ester (pale yellow oil, 2.15 g, quantitative). $C_{12}H_{12}O_3$; MW: 204.23; LCMS (method A) RT 1.40 min; ES 227 (25%, MNa$^+$), 205 (25%, MH$^+$), 173 (100%); IR: 2952, 1734, 1710, 1608, 1436 cm$^{-1}$; $^1$H NMR (400 MHz, CDCl$_3$) 7.78 (1H, d), 7.61 (1H, t), 7.47 (1H, d), 7.39 (1H, t), 3.70 (3H, s), 3.47 (1H, dd), 2.95-3.08 (2H, m), 2.89 (1H, dd), 2.63 (1H, dt) ppm. The compound was used without further purification for the next step Example I6(b)

methyl 2-(5-fluoro-1-oxo-indan-2-yl)acetate (H2)

The compounds in this example were synthesized by a known method described in Journal of Agricultural and Food Chemistry (1997), 45(6), 2278-2283 and Journal of Agricultural and Food Chemistry (1992), 40(7), 1230-5.

Step 1: 5-fluoro-1-oxo-indane-2-carboxylate

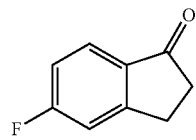
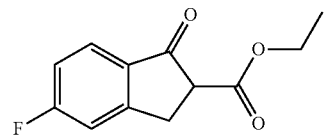

Sodium hydride (800 mg, 19.9 mmol, 60% in mineral oil) was washed with HPLC grade hexane (twice). Dry Benzene (4.2 ml) and diethyl carbonate (1.57 g, 1.6 ml, 13.3 mmol) were added and the resulting solution was refluxed for one hour (the reaction mixture turned green). 5-Fluoro-indanelone (1.0 g, 6.66 mmol) in benzene (2.7 ml) was added slowly to the refluxing solution over 45 mins. The resulting reaction mixture was refluxed for additional one hour. After completion of the reaction, acetic acid/water (50/50, approx 20 ml) were added until whole solid dissolved (pH-5). Aqueous layer was extracted three times with benzene. Combined organic part were washed with water, sat brine, dried over sodium sulphate and evaporated to dryness. Crude purified by column chromatography using ethyl acetate/hexane (5%) to yield desired product (1.3 g, 94%).

Step 2: Ethyl 2-(2-ethoxy-2-oxo-ethyl)-5-fluoro-1-oxo-indane-2-carboxylate

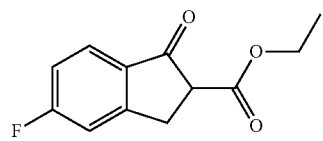
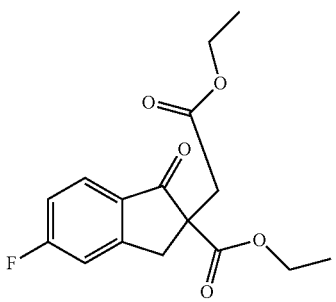

A mixture of ethyl 5-fluoro-1-oxo-indane-2-carboxylate (1.4 g, 6.3 mmol), sodium hydride (278 mg, 6.9 mmol, 60% in mineral oil) and DMF (dry, 2.5 ml) was heated to 65° C. for one hour. A solution of bromo ethylester (1.15 g, 0.8 ml, 6.9 mmol) in dry DMF (4.0 ml) was added at the same temperature and heating was continued for additional 3 h. After complete the reaction, reaction mass was evaporated to dryness, 5 ml water was added and the suspension was extracted with ethyl acetate (25 ml×3). Combined organic layer was washed with brine, dried over sodium sulphate, evaporated and subjected to column chromatography using ethyl acetate/hexane (15%) to yield a desired product (1.3 g, 72%).

Step 3: (5-Fluoro-1-oxo-indan-2-yl)-acetic acid

Ethyl 2-(2-ethoxy-2-oxo-ethyl)-5-fluoro-1-oxo-indane-2-carboxylate (500 mg, 1.6 mmol) was suspended in 1.4 ml mixture of 6 N HCl: acetic acid (1:1) and heated to reflux for 3 h. Reaction was monitored by TLC. Reaction mass was evaporated to dryness, 10 ml water was added and extracted with ethyl acetate (40 ml×3). Organic layer was washed with sat brine, dried over sodium sulphate. Crude product was washed with hexane to obtain a desired product (280 mg, 82%).

Step 4: methyl 2-(5-fluoro-1-oxo-indan-2-yl)acetate H2

(5-Fluoro-1-oxo-indan-2-yl)-acetic acid (280 mg, 1.3 mmol) was taken in 10 ml methanol (HPLC grade), cooled to 0° C. and 0.5 ml of conc. sulfuric acid was added drop wise into the solution and heated to reflux for 5 h. Reaction was monitored by TLC. After completion reaction mass was evaporated, 10 ml water was added and extracted with ethyl acetate (25 ml×3). Ethyl acetate part was washed with saturated aqueous sodium bicarbonate, brine, dried (sodium sulphate) and concentrated under reduced pressure. Crude was purified by column chromatography using acetone/hexane (8%) to yield a desired product H2 (230 mg, 77%).

This method was used to prepare the compound H2 to H8 (table H).

Example I6(c)

(1-Oxo-4-bromo-indan-2-yl)-acetic acid methyl ester H9

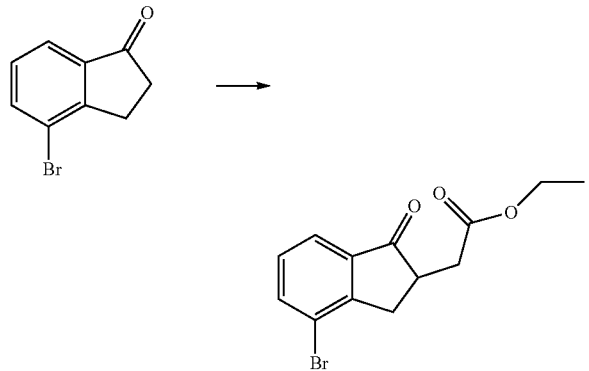

To a solution of 4-bromoindanone (15.8 g, 75 mmol) at −78° C. was added LiHMDS (1 M in THF, 90 mL). The slight brown solution was allowed to warm up to 0° C., and was cooled again to −75° and ethyl 2-bromoacetate (9.1 mL, 82 mmol) was added dropwise. The mixture was allowed to warm up over night (−75° C. to −20° C. over 12 h). The mixture was quenched with sat. ammonium chloride and was extracted with ethyl acetate. Flash chromatography give 19.5 g of the title compound in a mixture with the starting indanone ethyl 2-[4-bromo-2-(2-ethoxy-2-oxo-ethyl)-1-oxo-indan-2-yl]acetate H9 and which was used without further purification for the next step (purity, 60% of the desired product).

This method was used to prepare the compounds H9 and H10 (table H).

Example I7

3,3a,4,8b-Tetrahydro-1H-indeno[1,2-b]pyrrol-2-one

Example I7(a)

3,3a,4,8b-Tetrahydro-1H-indeno[1,2-b]pyrrol-2-one G1

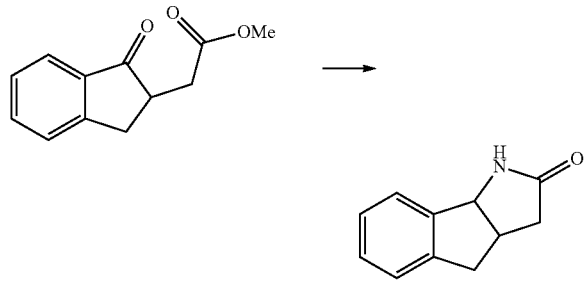

Method A

A solution of ammonium acetate (3.77 g, 48.9 mmol) was coevaporated in anhydrous methanol. Then, (1-Oxo-indan-2-yl)-acetic acid methyl ester H1 (1.00 g, 4.89 mmol) in methanol (40 mL) was added followed by molecular sieves (4.9 g). The solution was stirred for 30 min and sodium cyanoborohydride (0.92 g, 14.9 mmol) was added. The suspension was refluxed for 40 h. The solution was filtered through celite. A saturated solution of sodium hydrogenocarbonate was added and the solution was extracted with ethyl acetate (3*50 mL). The combined organic layers were washed with hydrogen chloride (1N), brine, dried and concentrated. The residue was purified by flash chromatography eluting with ethyl acetate and then ethyl acetate/methanol (95/5) to give 3,3a,4,8b-tetrahydro-1H-indeno[1,2-b]pyrrol-2-one G1 (White solid, 300 mg, 35%). LCMS (method A) RT 1.17; ES 196, 174; IR 3233, 1689 cm$^{-1}$; Mp: 150-153° C.; $^1$H NMR (400 MHz, CD$_3$OD) δ 7.34 (1H, d), 7.12-7.27 (3H, m), 5.04 (1H, d), 3.22-3.37 (2H, m), 2.83 (1H, d), 2.70 (1H, dd), 2.15 (1H, dd) ppm.

Method B

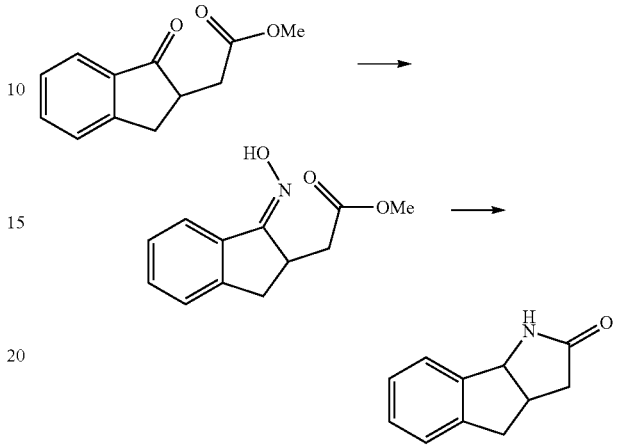

To a solution of 1-oxo-indan-2-yl-acetic acid methyl ester H1 (8.55 g, 41.89 mmol) in methanol (100 mL) was added sodium acetate (5.15 g, 62.8 mmol) and hydroxylamine hydrochloride (4.36 g, 62.8 mmol). The solution was heated to 65° C. for 12 h, diluted with water, extracted with ethyl acetate, washed with brine, dried and concentrated to give the corresponding oxime (8.00 g, 87%). The residue was taken up in acetic acid (70 mL) and heated to 60° C. Then, zinc dust (23.8 g, 364 mmol) was added protionwise, keeping the temperature under 80° C. The solution was stirred for 30 min at 60° C. and was then filtered.

Water was added to the filtrate and the solution was neutralized with solid potassium carbonate until pH reaches 7. The solution was extracted with dichloromethane, washed with aqueous HCl (1 N), dried and concentrated to give the lactame G1 (3.9 g, 61%) as a white solid. The data are identical to method A.

This method was used to prepare compounds G1 to G10 (table G).

Example I7(b)

7-nitro-3,3a,4,8b-tetrahydro-1H-indeno[1,2-b]pyrrol-2-one

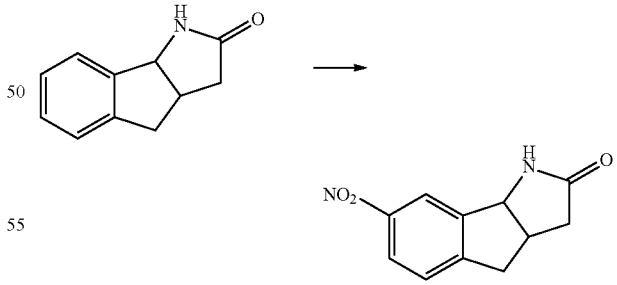

Sulphuric acid (72 mL) was added to a cooled mixture of nitric acid (63.5 mmol, 4.4 mL) and water (11.3 mL), and the mixture was added dropwise to a cold (2-8° C.) suspension of 3,3a,4,8b-tetrahydro-1H-indeno[1,2-b]pyrrol-2-one (10 g, 57.7 mmol) in nitromethane (100 mL). The mixture was stirred 1.5 h at 2-8° C. after end of addition, and poured onto a mixture of ice and water (1 L). The white suspension was stirred for one hour, filtered and washed with water. The white solid was suspended in 1 L of ethyl acetate, dried and concentrated under vacuum. 7-nitro-3,3a,4,8b-tetrahydro-1H-indeno[1,2-b]pyrrol-2-one (9.2 g, 73%) was obtained. $^1$H NMR (400 MHz, CD$_3$OD) δ 8.16-8.08 (2H, m), 7.39 (1H, d), 6.89 (1H, brs), 5.09 (1H, d), 3.49-3.37 (2H, m), 2.93 (1H, d), 2.78 (1H, dd), 2.26 (1H, dd) ppm.

Example I8

2-Oxo-3,3a,4,8b-tetrahydro-2H-indeno[1,2-b]pyrrole derivatives

Example I8(a)

2-Oxo-3,3a,4,8b-tetrahydro-2H-indeno[1,2-b]pyrrole-1-carboxylic acid tert-butyl ester F1

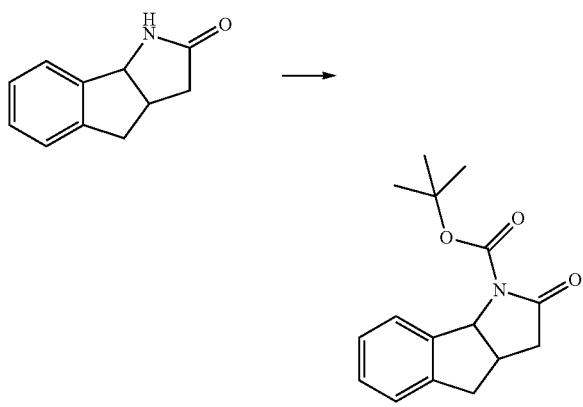

To a suspension of 3,3a,4,8b-tetrahydro-1H-indeno[1,2-b]pyrrol-2-one G1 (0.100 g, 0.578 mmol) in anhydrous acetonitrile (10 mL) was added dimethylaminopyridine (0.007 mg, 0.057 mmol), triethylamine (0.161 mL, 1.15 mmol) and di-t-butyl dicarbonate (245 mmol, 1.15 mmol in 1 mL of dichloromethane). The solution was stirred at room temperature for 6 h. The solution was diluted with ethyl acetate and washed with hydrogen chloride (1M) and brine. The combined organic layers were dried and concentrated. The residue was purified by flash chromatography eluting with ethyl acetate and cyclohexane (7/3) to give of gummy oil F1 (160 mg. quant.). C$_{16}$H$_{19}$NO$_3$; MW: 273.33; LCMS (method B) RT 1.74 min; ES: 296 (MNa$^+$), 174 (MH$^+$-Boc), 129; IR: 2978, 1782, 1747, 1709 cm$^{-1}$; $^1$H NMR (400 MHz, CDCl$_3$) δ7.57 (1H, d), 7.19-7.34 (3H, m), 5.62 (1H, d), 3.08-3.26 (2H, m), 2.84 (1H, d), 2.78 (1H, dd), 2.29 (1H, dd), 1.63 (9H, s) ppm.

This procedure was used to prepare compounds F1 to F10 (Table F).

Example I8(b)

Tert-butyl 5-cyano-2-oxo-3,3a,4,8b-tetrahydroindeno[1,2-b]pyrrole-1-carboxylate F11

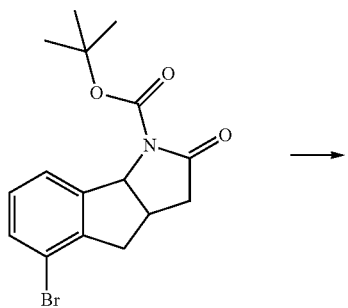

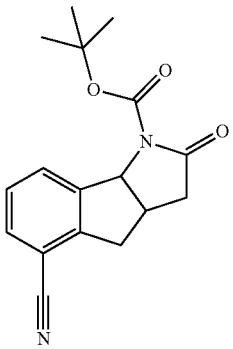

To a solution of tert-butyl 5-bromo-2-oxo-3,3a,4,8b-tetrahydroindeno[1,2-b]pyrrole-1-carboxylate F9 (1.5 g, 4.25 mmol) in DMF (30 mL) was added Pd(PPh$_3$)$_4$ (751 mg, 0.63 mmol) and Zn(CN)$_2$ (1.00 g, 8.51 mmol). The solution was stirred at 100° C. for 16 h. After cooling, water was added and the solution was extracted with ethyl acetate. The organic layer was washed with brine three times, dried and concentrated. The crude material was dissolved in 50 ml acetonitrile in which were added Boc$_2$O (5.5 g, 25.2 mmol), NEt$_3$ (6 ml), and DMAP (520 mg, 4.26 mmol). The resulting mixture was stirred for 16 h. The dark brown solution was concentrated under vacuum, and the residue was dissolved in ethyl acetate. The organic layer was washed twice with HCl (1N), brine, dried and concentrated under vacuum. The residue was purified by flash chromatography eluting with ethyl acetate and cyclohexane (10/90 to 30/70 over 30 min.) to give 880 mg of the desired compound F11 as a beige gum (69%). LCMS (method E): 0.87 min; ES+: 619 [2M+Na].

This method was used to prepare compounds F12 from F10 and F11 from F9 (Table F).

Example I8(c)

Tert-butyl 8-allyl-2-oxo-3,3a,4,8b-tetrahydroindeno[1,2-b]pyrrole-1-carboxylate F14

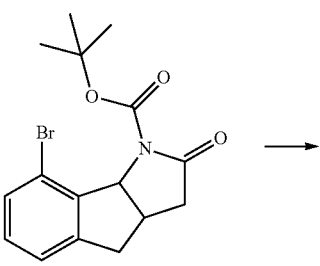

A solution tert-butyl 8-bromo-2-oxo-3,3a,4,8b-tetrahydroindeno[1,2-b]pyrrole-1-carboxylate (Example F10, 700 mg), Pd(PPh$_3$)$_4$ (280 mg, 0.12 equiv.), allyltributylstannate (1.65 g, 2.5 equiv.) in toluene (17 mL) was degassed and stirred at reflux over night. The solvent was removed under vacuum. The residue was taken up in acetonitrile (40 mL) and washed twice with n-hexane. The acetonitrile was removed in vacuo and the residue was purified by flash chromatography eluting with ethyl acetate and cyclohexane (1 to 25%) to give 350 mg of the desired products (mixture of allyl and isomer) F14: LCMS (method E), RT: 1.06 min, [ES+[377, M+CH$_3$CN+Na].

This method was used to prepare compounds F13 from F9 and F14 from F10 (Table F)

Example I8(d)

Tert-butyl-8-propyl-2-oxo-3,3a,4,8b-tetrahydroindeno[1,2-b]pyrrole-1-carboxylate F15

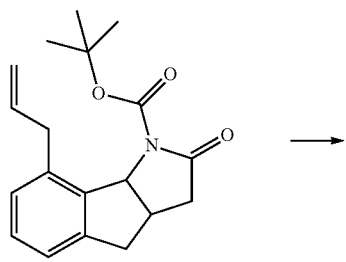

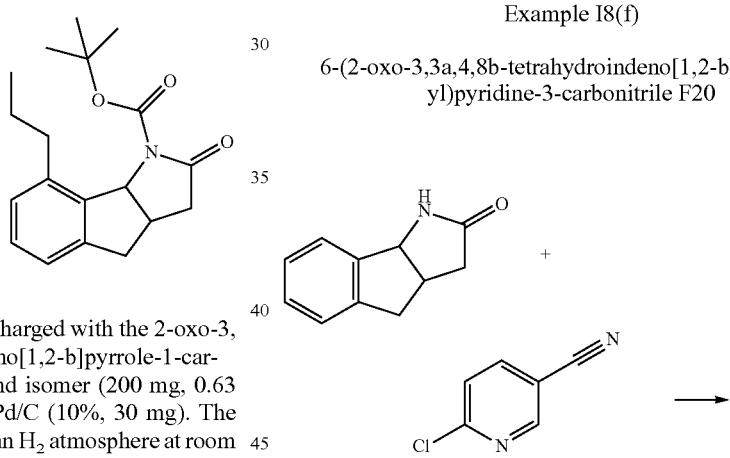

A flask flushed with Argon was charged with the 2-oxo-3,3a,4,8b-tetrahydro-2H-4-allyl-indeno[1,2-b]pyrrole-1-carboxylic acid tert-butyl ester F14 and isomer (200 mg, 0.63 mmol), ethyl acetate (4 mL) and Pd/C (10%, 30 mg). The black suspension was stirred under an H$_2$ atmosphere at room temperature for 72 h. The suspension was then filtered on a Celite pad, and the filtrate was concentrated under vacuum, purified by flash chromatography with a gradient of ethyl acetate in cyclohexane of 1 to 10%, to give the desired compound F15 as a colourless oil (120 mg, 60%). LCMS (method E): 1.14 min; ES+: 338 (M+Na$^+$).

Example I8(e)

1-(4-chlorophenyl)-3,3a,4,8b-tetrahydroindeno[1,2-b]pyrrol-2-one F16

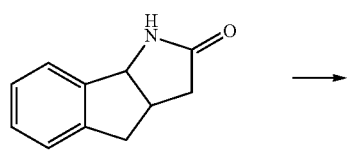

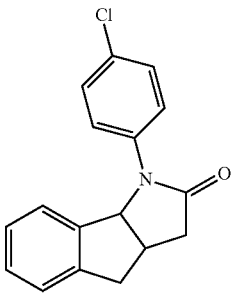

To a solution of tetrahydro-1H-indeno[1,2-b]pyrrol-2-one (1.00 g, 5.77 mmol) in water (3 mL) was added copper (I) oxide (167 mg), p-chloroiodobenzene (1.38 g, 5.77 mmol), tetrabutylammonium bromide (0.372 g, 1.15 mmol) and potassium phosphate (2.45 g, 11.5 mmol). The suspension was vigorously stirred at 130° C. overnight. The mixture was cooled down and diluted with dichloromethane. The solid were filtered off and the organic layer was dried and concentrated. The residue was purified by flash chromatography with a gradient of ethyl acetate in cyclohexane of 1 to 60%, to give the desired product F16 (600 mg, 39%). LCMS (method A) 1.72 min; ES+: 284 (M+H$^+$).

This procedure was used to prepare compound F16-F19.

Example I8(f)

6-(2-oxo-3,3a,4,8b-tetrahydroindeno[1,2-b]pyrrol-1-yl)pyridine-3-carbonitrile F20

To a suspension of 3,3a,4,8b-tetrahydro-1H-indeno[1,2-b]pyrrol-2-one (1 g, 5.77 mmol) in toluene (15 ml) was added sodium hydride (0.254 g, 6.35 mmol) at 0° C. The batch was warmed to room temperature and 2-chloro-5-cyanopyridine (0.824 g, 5.77 mmol) was added. The batch was stirred at 95° C. for 2 h. After cooling, the batch was added to ice water and extracted with ethyl acetate (2×). The combined organic phases were concentrated and the residue was purified by column chromatography (hexane/ethyl acetate 7/3) to give 6-(2-oxo-3,3a,4,8b-tetrahydroindeno[1,2-b]pyrrol-1-yl)pyridine-3-carbonitrile F20 (1.00 g, 63%). LCMS (method A) 1.68 min; ES+: 276 (M+H+).

Example I8(g)

((3aR,8bS)-1-thiazol-2-yl-3,3a,4,8b-tetrahydroindeno[1,2-b]pyrrol-2-one F21

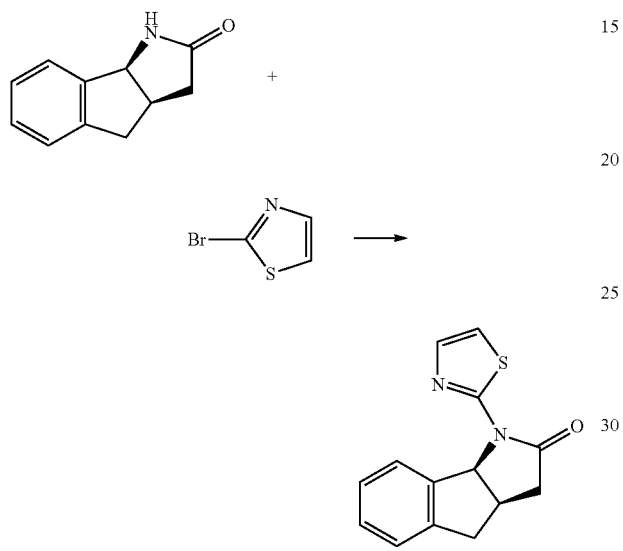

To a solution of (3aR,8bS)-3,3a,4,8b-tetrahydro-1H-indeno[1,2-b]pyrrol-2-one (0.500 g, 2.89 mmol) in dioxane (6 mL) was added potassium phosphate (1.26 g, 5.77 mmol), copper iodide (0.055 g, 0.289 mmol), 2-bromo thoazole (0.473 g, 2.89 mmol) and N,N'-dimethylethane-1,2-diamine (0.0254 g, 0.288 mmol). The yellow solution was heated to reflux overnight. The suspension was then diluted with ethyl acetate and filtered. The solvents were removed in vacuo and the residue was purified by flash chromatography eluting with cyclohexane and ethyl acetate (0-50%) to give the title compound as a colourless oil ((3aR,8bS)-1-thiazol-2-yl-3,3a,4,8b-tetrahydroindeno[1,2-b]pyrrol-2-one F21 (0.390 g, 1.52 mmol, 52.7% Yield). LCMS (method A) 1.66 min; ES+: 257 (M+H+).

Example I8(h)

3aR,8bS)-1-allyl-3,3a,4,8b-tetrahydroindeno[1,2-b]pyrrol-2-one F22

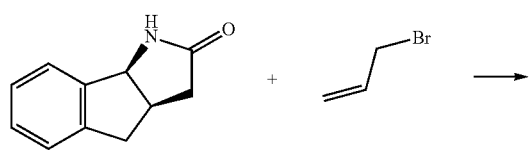

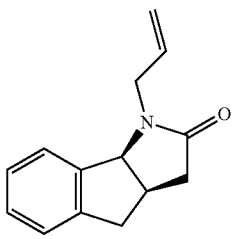

To a solution of (3aR,8bS)-3,3a,4,8b-tetrahydro-1H-indeno[1,2-b]pyrrol-2-one (1.00 g, 5.77 mmol) in DMF (10 mL) was added at 0° C. sodium hydride (60% in mineral oil, 0.254 g, 6.35 mmol). The solution was stirred for 1 h at 0° C. and allyl bromide (1.41 g, 2 equiv., 1.01 mL, 11.5 mmol) was added. The solution was stirred for 18 h at room temperature and water was added. The mixture was extracted with ethyl acetate and washed with water and brine. The solvents were removed in vacuo and the residue was purified by flash chromatography eluting with cyclohexane and ethyl acetate (50:50) to give (3aR,8bS)-1-allyl-3,3a,4,8b-tetrahydroindeno[1,2-b]pyrrol-2-one F22 (0.910 g, 0.910 g, 4.27 mmol, 73.9% Yield) as a colourless oil. LCMS (method A) 1.51 min; ES+: 214 (M+H+).

The compounds F23 to F25 were prepared according to this procedure using 4-fluorobenzylchloride, 2-bromoacetonitrile, ethylchloroformate as alkylating reagent.

Example I8(i)

tert-butyl (3aR,8bS)-2,4-dioxo-3a,8b-dihydro-3H-indeno[1,2-b]pyrrole-1-carboxylate F26

To a solution of 2-oxo-3,3a,4,8b-tetrahydro-2H-indeno[1,2-b]pyrrole-1-carboxylic acid tert-butyl ester F1 (5.00 g, 18.2 mmol) in acetone (90 mL) and water (20 mL) was added KMnO4 (14.7 g, 93 mmol). The solution was stirred for 48 h at room temperature and filtered. The solution was concentrated to half the volume and sodium thiosulfate solution was added (2%, 50 mL). The solution was extracted with ethylacetate, washed with brine, dried and concentrated. The residue was purified by flash chromatography eluting with cyclohex-

Example I8(j)

tert-butyl (3aR,4R,8bS)-4-hydroxy-2-oxo-3,3a,4,8b-tetrahydroindeno[1,2-b]pyrrole-1-carboxylate F27

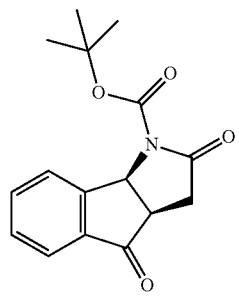 

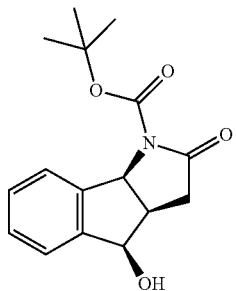

To a solution of tert-butyl (3aR,8bS)-2,4-dioxo-3a,8b-dihydro-3H-indeno[1,2-b]pyrrole-1-carboxylate F 26 (1.60 g, 5.56 mmol) in ethanol (20 mL) and THF (20 mL) was added at 0° C. NaBH₄ (0.316 g, 8.15 mmol). The solution was stirred for 2 h at 0° C. 1M HCl was carefully added and the solution was concentrated in vacuo. The residue was partitioned between ethyl acetate and water and extracted with ethyl acetate. The combined organic layers were washed with brine, dried and concentrated. The residue was purified by flash chromatography (2/1 cyclohexane/ethyl acetate) to give tert-butyl (3aR,4R,8bS)-4-hydroxy-2-oxo-3,3a,4,8b-tetrahydroindeno[1,2-b]pyrrole-1-carboxylate F27 (800 mg, 50%). LCMS (method E): 0.78 min; ES+: 601 (2M+Na⁺).

Example I8(k)

tert-butyl (3aR,4S,8bS)-4-fluoro-2-oxo-3,3a,4,8b-tetrahydroindeno[1,2-b]pyrrole-1-carboxylate F28

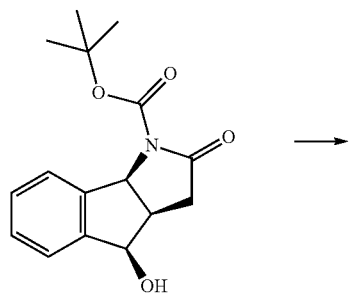

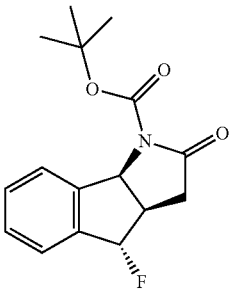

To a solution of tert-butyl (3aR,4R,8bS)-4-hydroxy-2-oxo-3,3a,4,8b-tetrahydroindeno[1,2-b]pyrrole-1-carboxylate (0.200 g, 0.691 mmol) in dichloromethane (1 equiv., 3 mL, 0.69 mmol) was added at 0° C. diethylaminosulfur trifluoride (0.913 mL, 6.91 mmol). The solution was stirred at 0° C. for 30 min. The reaction mixture was carefully quenched with NaHCO₃ sat. and extracted with dichloromethane. The organic layer was dried and concentrated. The residue was purified by flash chromatography (0-80% ethyl acetate in cyclohexane) to give the desired product F28 (0.150 g, 74%). LCMS (method A): 1.65 min; ES+: 605 (2M+Na⁺).

Example I8(l)

tert-butyl 4-acetoxy-2-oxo-3,3a,4,8b-tetrahydroindeno[1,2-b]pyrrole-1-carboxylate F29

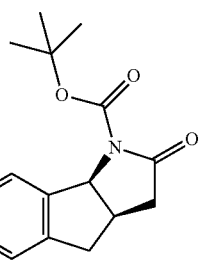 

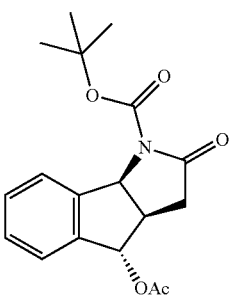

To a solution of tert-butyl 2-oxo-3,3a,4,8b-tetrahydroindeno[1,2-b]pyrrole-1-carboxylate (1.28 g, 4.68 mmol) in dichloromethane (9 mL) was added p-toluenesulfonamide (0.164 g, 0.937 mmol), (diacetoxyiodo)benzene (3.85 g, 11.7 mmol) and iodine (0.238 g, 0.937 mmol). The solution was heated at 60° C. under argon for 2 h. The solution was cooled down to room temperature and sat. sodium sulfite was added (2 mL). Water was added and the solution was extracted with dichloromethane (3*50 mL), dried and concentrated. The residue was purified by flash chromatography (10 to 90% ethyl acetate in cyclohexane) to give tert-butyl 4-acetoxy-2-oxo-3,3a,4,8b-tetrahydroindeno[1,2-b]pyrrole-1-carboxylate F29 (0.900 g, 58%) as a mixture of diastereoisomers (2:1 in favour of the trans). The isomers could not be separated. LCMS (method E): 0.90 min; ES+: 685 (2M+Na⁺).

Example I9

Synthesis of 3-[1-Dimethylamino-meth-(Z)-ylidene]-2-oxo-3,3a,4,8b-tetrahydro-2H-indeno[1,2-b]pyrrole-1-carboxylic acid tert-butyl ester E1

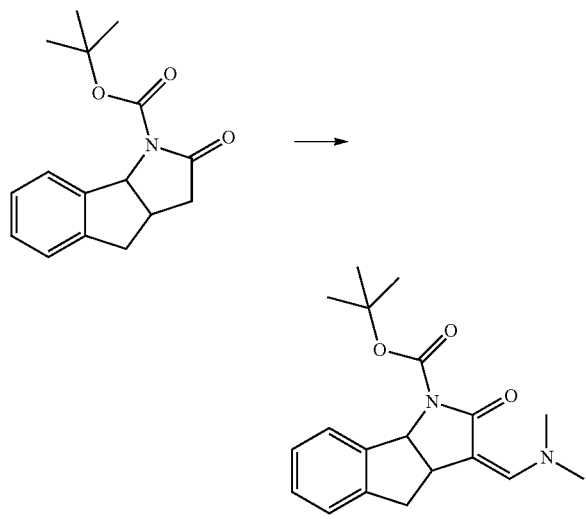

A solution of the 2-oxo-3,3a,4,8b-tetrahydro-2H-indeno[1,2-b]pyrrole-1-carboxylic acid tert-butyl ester F1 (160 mg, 0.586 mmol) in tert-butoxybis(dimethylamino)methane was heated at 75° C. for 4 h. The solution was diluted with ethyl acetate and washed with water, brine, dried and concentrated to give 3-[1-dimethylamino-meth-(Z)-ylidene]-2-oxo-3,3a,4,8b-tetrahydro-2H-indeno[1,2-b]pyrrole-1-carboxylic acid tert-butyl ester E1 (colourless solid, 190 mg, 98%). $C_{19}H_{24}N_2O_3$; MW: 328.41; LCMS (method A) RT 1.78 min; ES: 329 (MH$^+$), 273; $^1$H NMR (400 MHz, CDCl$_3$) δ 7.74 (1H, d), 7.15-7.26 (4H, m), 5.61 (1H, d), 3.99 (1H, td), 3.37 (1H, dd), 3.10 (6H, s), 3.06 (1H, dd), 1.60 (9H, s) ppm.

This method was used to prepare compounds E1 to E15 (Table E)

Example I10

Synthesis of 3-[1-Hydroxy-meth-(Z)-ylidene]-2-oxo-3,3a,4,8b-tetrahydro-2H-indeno[1,2-b]pyrrole derivatives

Example I10(a)

3-[1-Hydroxy-meth-(Z)-ylidene]-2-oxo-3,3a,4,8b-tetrahydro-2H-indeno[1,2-b]pyrrole-1-carboxylic acid tert-butyl ester D1

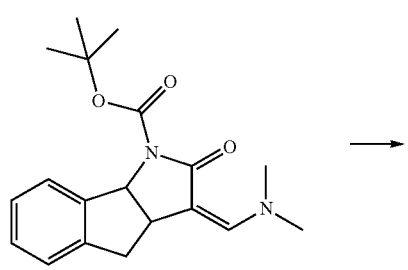

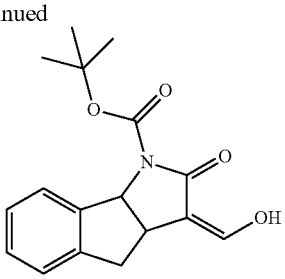

To a solution of 3-[1-dimethylamino-meth-(Z)-ylidene]-2-oxo-3,3a,4,8b-tetrahydro-2H-indeno[1,2-b]pyrrole-1-carboxylic acid tert-butyl ester E1 (190 mg, 0.579 mmol) in tetrahydrofurane (2 mL) was added hydrogen chloride (1M, 0.87 mL). The solution was stirred at room temperature for 3 h. The solution was diluted with ethyl acetate and washed with water, brine, dried and concentrated. The residue was triturated with ethyl acetate to give 3-[1-Hydroxy-meth-(Z)-ylidene]-2-oxo-3,3a,4,8b-tetrahydro-2H-indeno[1,2-b]pyrrole-1-carboxylic acid tert-butyl ester D1 (White powder, 140 mg, 80%). $C_{17}H_{19}NO_4$; MW: 301.35; LCMS (method A) RT 1.72 min; ES: 302 (MK), 246; $^1$H NMR (400 MHz, DMSO-d$_6$) δ 11.04 (1H, s), 7.54 (1H, d), 7.42 (1H, d), 7.13-7.31 (3H, m), 5.59 (1H, d), 3.70 (1H, m), 3.22 (1H, dd), 3.15 (1H, dd), 1.53 (10H, s) ppm.

This method was used to prepare compounds D1 to D10 and D25 (table D).

Example I10(b)

Synthesis of tert-butyl (3Z)-5-propyl-3-(dimethylaminomethylene)-2-oxo-4,8b-dihydro-3aH-indeno[1,2-b]pyrrole-1-carboxylate D11

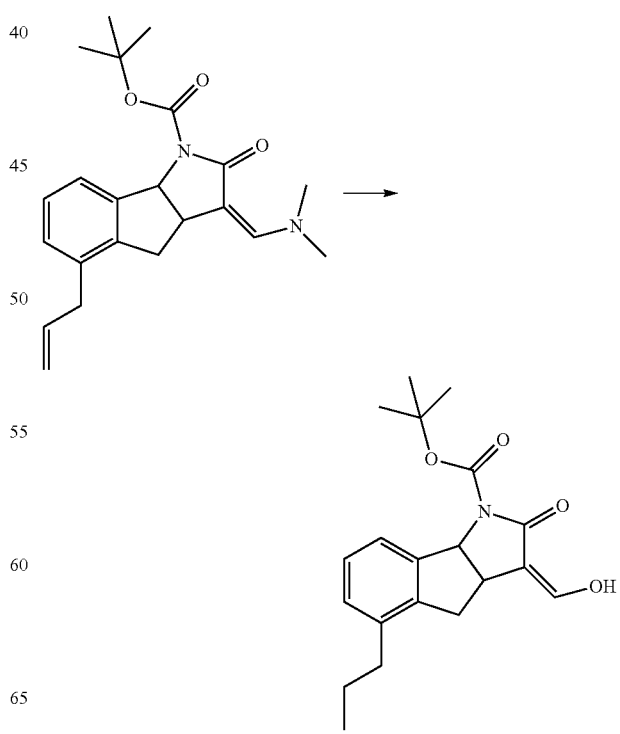

To a flask flushed with Argon was charged with tert-butyl (3Z)-5-allyl-3-(dimethylaminomethylene)-2-oxo-4,8b-dihydro-3aH-indeno[1,2-b]pyrrole-1-carboxylate D10 (98 mg, 0.29 mmol) and Pd/C (10%, 40 mg) and ethyl acetate (6 mL). To the black suspension was stirred under an H₂ atmosphere at room temperature for 24 h. The suspension was filtered on a Celite pad, and the yellow filtrate was concentrated under vacuum to give the title compound D11 as a brown gum (47 mg, 47%). LCMS (Method E): RT: 1.06 min; ES– 342 [M–H]

Example I10(c)

Synthesis of ethyl (3E)-3-(hydroxymethylene)-2-oxo-4,8b-dihydro-3aH-indeno[1,2-b]pyrrole-1-carboxylate D12

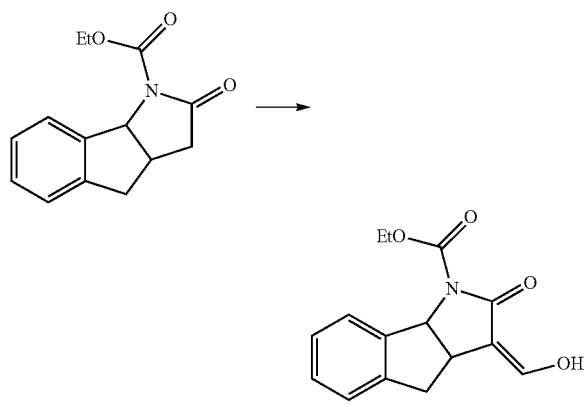

Ethyl 2-oxo-3,3a,4,8b-tetrahydroindeno[1,2-b]pyrrole-1-carboxylate (200 mg, 0.81 mmol) was dissolved in tetrahydrofuran (8 mL) was cooled to –78° C. Then, lithium bis(trimethylsilyl)amide (1 mol/L in THF, 1.22 mL, 1.22 mmol) was added. After 1 h at –78° C., ethyl formate (0.198 mL, 2.446 mmol) was added. The mixture was stirred for another 30 min and then allowed to warm to room temperature. After another 30 min, water was added. The mixture was extracted with diethylether, the pH of the aqueous layer was adjusted to 1 and the solution was extracted with EtOAc (2*20 mL), dried (Na₂SO₄) and concentrated to give a colourless oil ethyl (3E)-3-(hydroxymethylene)-2-oxo-4,8b-dihydro-3aH-indeno[1,2-b]pyrrole-1-carboxylate D12 (120 mg, 54%) which was used without further purification in the next step. LCMS (Method A): RT: 1.53 min; ES– 272 [M–H]

The following compounds were prepared according to this procedure D12-D21, D23 and D24.

Example D22

Synthesis of (3E)-1-acetyl-3-(hydroxymethylene)-4,8b-dihydro-3aH-indeno[1,2-b]pyrrol-2-one D22

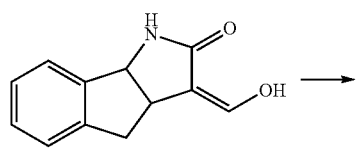

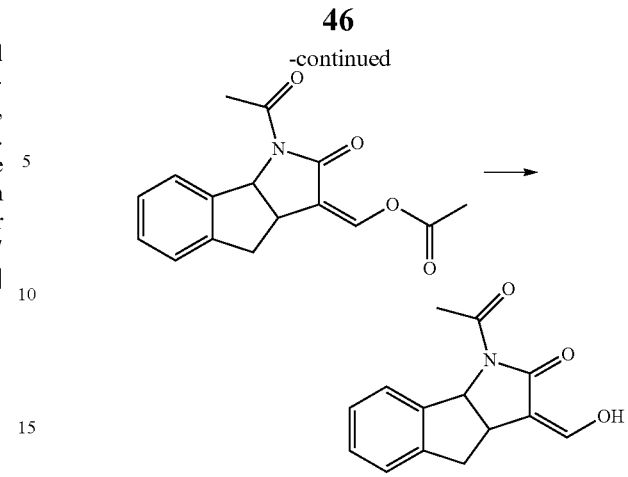

To a solution of (3E)-3-(hydroxymethylene)-1,3a,4,8b-tetrahydroindeno[1,2-b]pyrrol-2-one (100 mg, 0.497 mmol) in dichloromethane (5 mL, 0.497 mmol) was added N,N-dimethylpyridin-2-amine (6 mg, 0.05 mmol), N,N-diethylethanamine (0.20 mL, 1.49 mmol), acetic anhydride (0.152 g, 1.49 mmol). The solution was stirred for 24 h at room temperature. The mixture was diluted with dichloromethane and washed with 1N HCl. The organic layer was dried and concentrated and the residue was purified by flash chromatography (0-100% EtOAc in CyH) to give [(E)-(1-acetyl-2-oxo-4,8b-dihydro-3aH-indeno[1,2-b]pyrrol-3-ylidene)methyl] acetate (45 mg, 31%) (LCMS (Method A): RT: 1.69 min; ES+286 (M+H⁺). To a solution of the previous material (40 mg, 0.14 mmol) in methanol (1 mL) was added potassium carbonate (0.019 g, 0.14 mmol). The solution was stirred for 30 min and 1N HCl was added (2 drops). Water was added (20 mL) and the solution was extracted with EtOAc (2*20 mL), dried and concentrated to give a white solid (35 mg, quant.), which was used without further purification in the next step. LCMS (Method A): RT: 1.53 min; ES– 272 [M–H].

Example I11

Synthesis of 3-[1-Hydroxy-meth-(Z)-ylidene]-3,3a,4,8b-tetrahydro-1H-indeno[1,2-b]pyrrol-2-one (C1)

Method A:

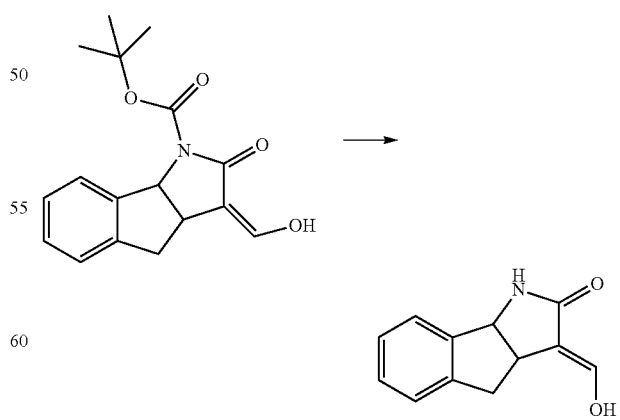

A solution of 3-[1-hydroxy-meth-(Z)-ylidene]-2-oxo-3,3a,4,8b-tetrahydro-2H-indeno[1,2-b]pyrrole-1-carboxylic acid tert-butyl ester D1 (0.400 g, 1.32 mmol) in dichloromethane (20 mL) was added trifluoroacetic acid (2 mL) at 0° C. The solution was stirred for 1 h. A saturated solution of sodium hydrogenocarbonate was added and the aqueous layer was extracted with dichloromethane. The combined organic layers were washed with a saturated solution of sodium hydrogenocarbonate, dried and concentrated in vacuo to give 3-[1-Hydroxy-meth-(Z)-ylidene]-3,3a,4,8b-tetrahydro-1H-indeno[1,2-b]pyrrol-2-one C1 (White solid, 271 mg, quant.). $C_{12}H_{11}NO_2$; MW: 201.23; LCMS (method A) RT 1.18 min; ES: 256 (MH$^+$+MeCN), 224 (MNa$^+$), 202 (MH$^+$); IR: 3264, 1678 cm$^{-1}$; $^1$H NMR (400 MHz, DMSO-d$_6$) δ 10.00 (1H, s), 7.16-7.38 (4H, m), 7.13 (1H, d), 4.94 (1H, d), 3.68-3.82 (1H, m), 3.31 (2H, dd), 3.01 (1H, dd) ppm.

This method was used to prepare compounds C1 to C10 (Table C)

Method B:

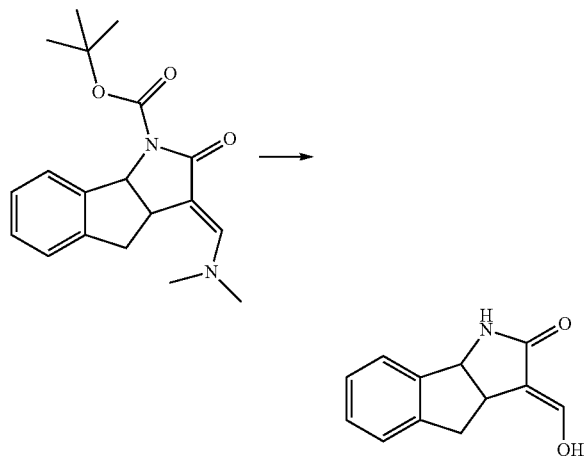

To a solution of 3-[1-dimethylamino-meth-(Z)-ylidene]-2-oxo-3,3a,4,8b-tetrahydro-2H-indeno[1,2-b]pyrrole-1-carboxylic acid tert-butyl ester D1 (1.68 g, 4.63 mmol) in dioxane (50 mL) was added HCl (37%, 8.37 mL). The solution was stirred overnight at room temperature and was then diluted with water, extracted with ethyl acetate, washed with brine, dried and concentrated to give 3-[1-Hydroxy-meth-(Z)-ylidene]-3,3a,4,8b-tetrahydro-1H-indeno[1,2-b]pyrrol-2-one C1 identical to method A (0.85 g, 78%).

This method was used to prepare: C1, C11 to C14 (Table C).

Example P1 and P2

Synthesis of the diastereoisomer of (3aR*,8bS*,5'R*)-3-[1-(4-Methyl-5-oxo-2,5-dihydro-furan-2-yloxy)-meth-(E)-ylidene]-3,3a,4,8b-tetrahydro-1H-indeno[1,2-b]pyrrol-2-one (P1) and the diastereoisomer of (3aR*,8bS*,5'S*)-3-[1-(4-Methyl-5-oxo-2,5-dihydro-furan-2-yloxy)-meth-(E)-ylidene]-3,3a,4,8b-tetrahydro-1H-indeno[1,2-b]pyrrol-2-one (P2)

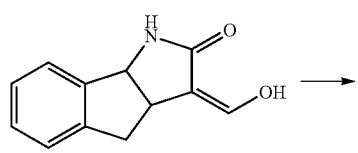

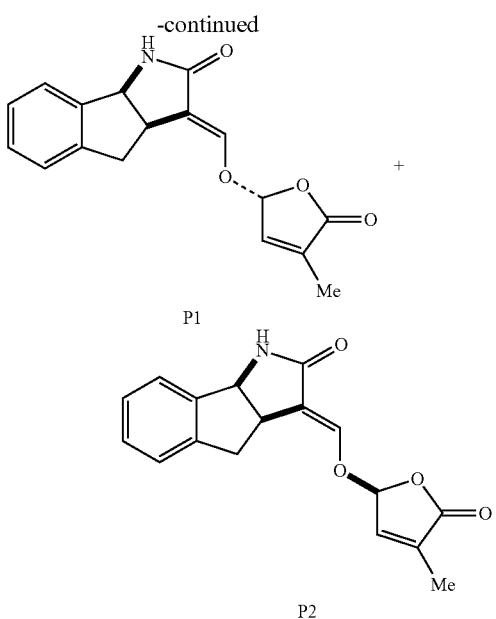

To a solution of 3-[1-Hydroxy-meth-(Z)-ylidene]-3,3a,4,8b-tetrahydro-1H-indeno[1,2-b]pyrrol-2-one C1 (0.130 g, 0.646 mmol) in dimethylformamide (5 mL) cooled at 0° C. was added potassium tert butoxide (0.086 g, 0.711 mmol). The solution was stirred for 10 min. and a solution of bromo butenolide (0.137 mg, 0.775 mmol, prepared according to Johnson & all, J.C.S. Perkin I, 1981, 1734-1743) in tetrahydrofurane (1 mL) was added. The solution was stirred at 0° C. for 3 h. The solution was partitioned between ethyl acetate and water and the aqueous layer was extracted with ethyl acetate. The combined organic layer was washed with brine and concentrated. The residue was purified by flash chromatography eluting with cyclohexane and ethyl acetate (1/4). Two diastereoisomers were obtained:

diastereoisomer of (3aR*,8bS*,5'R*)-3-[1-(4-Methyl-5-oxo-2,5-dihydro-furan-2-yloxy)-meth-(E)-ylidene]-3,3a,4,8b-tetrahydro-1H-indeno[1,2-b]pyrrol-2-one P1 (less polar, 50 mg, 26%); $C_{17}H_{15}NO_4$; MW: 297.31; Mp 200° C.; LCMS (method A) RT 1.52 min; ES: 339 (MH$^+$+MeCN), 298 (MH$^+$); $^1$H NMR (400 MHz, CDCl$_3$) δ 7.18-7.34 (5H, m), 6.96 (1H, s), 6.94 (1H, br. s.), 6.16 (1H, s), 5.12 (1H, d), 3.91 (1H, tt), 3.46 (1H, dd), 3.09 (1H, dd), 2.02 (3H, s) ppm.

diastereoisomer of (3aR*,8bS*,5'S*)-3-[1-(4-Methyl-5-oxo-2,5-dihydro-furan-2-yloxy)-meth-(E)-ylidene]-3,3a,4,8b-tetrahydro-1H-indeno[1,2-b]pyrrol-2-one P2 (more polar, 50 mg, 26%); $C_{17}H_{15}NO_4$; MW: 297.31; mp 213° C.; LCMS (method A) RT 1.51 min; ES: 339 (MH$^+$+MeCN), 298 (MH$^+$); $^1$H NMR (400 MHz, CDCl$_3$) δ 7.11-7.38 (5H, m), 6.96 (1H, s), 6.73 (1H, br. s.), 6.15 (1H, s), 5.12 (1H, d), 3.91 (1H, tt), 3.44 (1H, dd), 3.08 (1H, dd), 2.02 (3H, s) ppm.

The compounds A2 to A27 and B2 to B27 were prepared according to the same procedure. A2-A27 are the less polar diastereoisomers (see Table A); B2-27 are the more polar diastereoisomers (see Table B).

Example A27

Synthesis of (3E)-1-[(4-fluorophenyl)methyl]-3-[(4-methyl-5-oxo-2H-furan-2-yl)oxymethylene]-4,8b-dihydro-3aH-indeno[1,2-b]pyrrol-2-one A27 and of (3E)-1-[(4-fluorophenyl)methyl]-3-[(4-methyl-5-oxo-2H-furan-2-yl)oxymethylene]-4,8b-dihydro-3aH-indeno[1,2-b]pyrrol-2-one B27

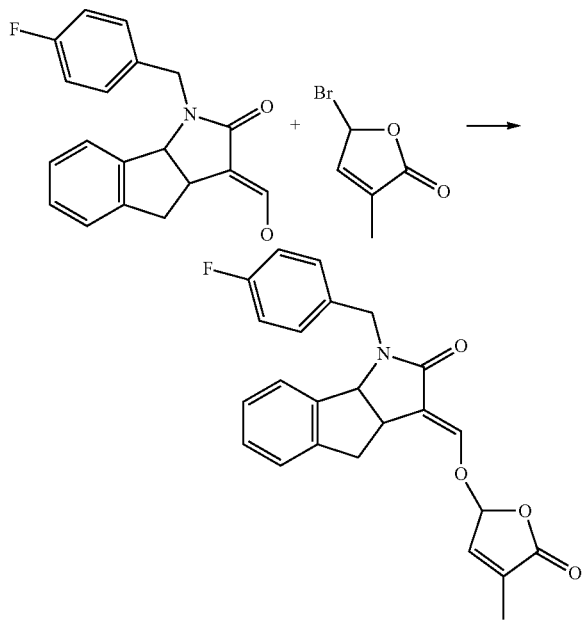

To a solution of (3E)-1-[(4-fluorophenyl)methyl]-3-(hydroxymethylene)-4,8b-dihydro-3aH-indeno[1,2-b]pyrrol-2-one (60 mg, 0.1940 mmol) in dichloromethane (10 mL) was added 2-bromo-4-methyl-2H-furan-5-one (51 mg, 0.291 mmol) and Hunig's base (0.064 mL, 0.39 mmol). The solution was stirred overnight at room temperature and the solvent was removed in vacuo. The residue was purified by flash chromatography eluting with cyclohexane and ethyl acetate (1:4) to give the desired product as a mixture of diastereoisomers (3E)-1-[(4-fluorophenyl)methyl]-3-[(4-methyl-5-oxo-2H-furan-2-yl)oxymethylene]-4,8b-dihydro-3aH-indeno[1,2-b]pyrrol-2-one A27 and B27 (30 mg, 38%). LCMS (method A) RT 1.85 min; ES: 406 (M+H+).

The compounds A28, B28, A29 and B29 were prepared according to this procedure (table A and B).

Example P3

Synthesis of 1-Methyl-(3aR*,8bS*,5'R*)-3-[1-(4-Methyl-5-oxo-2,5-dihydro-furan-2-yloxy)-meth-(E)-ylidene]-3,3a,4,8b-tetrahydro-1H-indeno[1,2-b]pyrrol-2-one

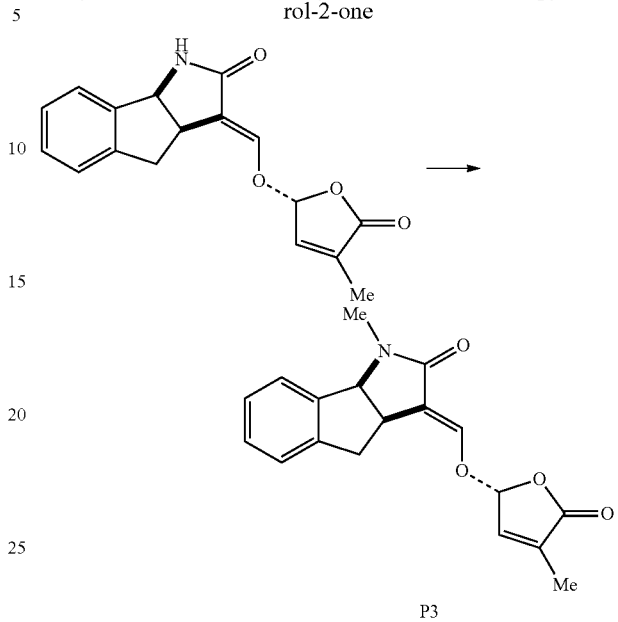

To a solution of diastereoisomer of (3aR*,8bS*,5'R*)-3-[1-(4-Methyl-5-oxo-2,5-dihydro-furan-2-yloxy)-meth-(E)-ylidene]-3,3a,4,8b-tetrahydro-1H-indeno[1,2-b]pyrrol-2-one P1 (23 mg, 0.077 mmol) in dimethylformamide (1 mL) was added sodium hydride (3.5 mg, 0.077 mmol) followed by methyl iodine (1 drop). The solution was stirred at 0° C. for 2 h and then 24 h at rt. The solution was partitioned between ethyl acetate and water and the aqueous layer was extracted with ethyl acetate. The combined organic layer was washed with brine and concentrated. The residue was purified by flash chromatography eluting with cyclohexane-ethyl acetate (1/4). The residue was triturated in pentane to give diastereoisomer of 1-Methyl-(3 aR*,8bS*,5'R*)-3-[1-(4-Methyl-5-oxo-2,5-dihydro-furan-2-yloxy)-meth-(E)-ylidene]-3,3a,4,8b-tetrahydro-1H-indeno[1,2-b]pyrrol-2-one P3 (White solid, 12 mg, 49%). $C_{18}H_{17}NO_4$; MW: 311.34; Mp 130-135° C.; LCMS (method A) RT 1.61 min; ES 312 (MK), 353 (MH++MeCN); 1H NMR (400 MHz, CDCl3) δ 7.41 (1H, d), 7.19-7.35 (5H, m), 6.95 (1H, t), 6.15 (1H, s), 4.90 (1H, d), 3.83 (1H, m), 3.48 (1H, dd), 3.01 (3H, s), 2.98 (1H, dd), 2.02 (3H, s) ppm.

TABLE A

Compounds of formula (I), less polar diastereoisomer (R2 = R3 = R5 = R7 = R8 = H, R6 = Me, W = O)

(I)

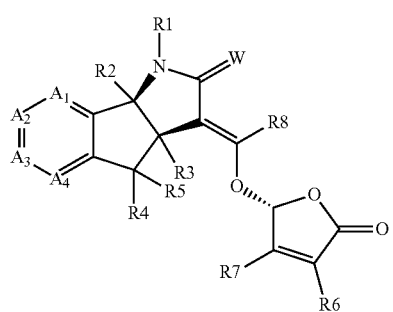

| Ex. | R1 | R4 | A1 | A2 | A3 | A4 | LCMS | RT | Mass |
|-----|-----|-----|------|------|------|------|------|------|---------|
| P1 | H | H | C—H | C—H | C—H | C—H | A | 1.52 | 298, M + H+ |
| P3 | Me | H | C—H | C—H | C—H | C—H | A | 1.61 | 312, M + H+ |

TABLE A-continued

Compounds of formula (I), less polar diastereoisomer (R2 = R3 = R5 = R7 = R8 = H, R6 = Me, W = O)

(I)

| Ex. | R1 | R4 | A$_1$ | A$_2$ | A$_3$ | A$_4$ | LCMS | RT | Mass |
|---|---|---|---|---|---|---|---|---|---|
| A2 | H | H | C—H | C—H | C—H | C—Br | E | 0.85 | 417, M + MeCN + H$^+$ |
| A3 | H | H | C—H | C—Me | C—H | C—H | E | 0.83 | 312, M + H$^+$ |
| A4 | H | H | C—H | C—H | C—OMe | C—H | E | 0.78 | 328, M + H$^+$ |
| A5 | H | H | C—H | C—H | C—H | C—Me | E | 0.82 | 312, M + H$^+$ |
| A6 | H | H | C—Br | C—H | C—H | C—H | E | 0.83 | 376, M + H$^+$ |
| A7 | H | H | C—H | C—H | C—H | C—CF$_3$ | E | 0.86 | 407, M + MeCN + H$^+$ |
| A8 | H | H | C—Me | C—H | C—H | C—H | E | 0.83 | 312, M + H$^+$ |
| A9 | H | H | C—H | C—H | C—F | C—H | E | 0.80 | 316, M + H$^+$ |
| A10 | H | H | C—H | C—H | C—Cl | C—H | E | 0.85 | 332, M + H$^+$ |
| A11 | H | H | C—H | C—H | C—H | CN | E | 0.72 | 364, M + MeCN + H$^+$ |
| A12* | H | H | C—CN | C—H | C—H | C—H | E | 0.72 | 323, M + H$^+$ |
| A13 | H | H | C—$^n$Pr | C—H | C—H | C—H | E | 0.94 | 340, M + H$^+$ |
| A14 | H | H | C—H | C—H | C—H | C—$^n$Pr | E | 0.92 | 340, M + H$^+$ |
| A15* | Boc | H | C—H | C—H | C—H | C—H | B | 1.91 | 420, M + Na$^+$ |
| A16* | 2-(5-cyanopyridyl) | H | C—H | C—H | C—H | C—H | A | 1.82 | 400, M + H$^+$ |
| A17 | phenyl | H | C—H | C—H | C—H | C—H | A | 1.78 | 374, M + H$^+$ |
| A18 | 4-Cl-phenyl | H | C—H | C—H | C—H | C—H | A | 1.86 | 408, M + H$^+$ |
| A19* | 4-CF$_3$-phenyl | H | C—H | C—H | C—H | C—H | A | 1.90 | 442, M + H$^+$ |
| A20 | 4-OMe-phenyl | H | C—H | C—H | C—H | C—H | A | 1.75 | 404, M + H$^+$ |
| A21 | CO$_2$Et | H | C—H | C—H | C—H | C—H | A | 1.69 | 370, M + H$^+$ |
| A22 | Ac | H | C—H | C—H | C—H | C—H | A | 1.69 | 340, M + H$^+$ |
| A23 | Boc | H | C—H | NO2 | C—H | C—H | E | 0.98 | 477, M + Cl– |
| A24* | Boc | OAc | C—H | C—H | C—H | C—H | A | 1.82 | 478, M + Na$^+$ |
| A25* | Boc | F | C—H | C—H | C—H | C—H | A | 1.78 | 438, M + Na$^+$ |
| A26 | 2-thiazolyl | H | C—H | C—H | C—H | C—H | A | 1.80 | 381, M + H$^+$ |
| A27* | 4-F-benzyl | H | C—H | C—H | C—H | C—H | A | 1.85 | 406, M + H$^+$ |
| A28* | CH$_2$CN | H | C—H | C—H | C—H | C—H | A | 1.51 | 337, M + H$^+$ |
| A29* | allyl | H | C—H | C—H | C—H | C—H | A | 1.70 | 338, M + H$^+$ |

*1/1 mixture of diastereoisomers with the corresponding compound B.

TABLE B

Compounds of formula (I), more polar diastereoisomer (R2 = R3 = R5 = R7 = R8 = H, R6 = Me, W = O)

(I)

| Ex. | R1 | R4 | A$_1$ | A$_2$ | A$_3$ | A$_4$ | LCMS | RT | Mass |
|---|---|---|---|---|---|---|---|---|---|
| P2 | H | H | C—H | C—H | C—H | C—H | A | 1.52 | 298, M + H$^+$ |
| B2 | H | H | C—H | C—H | C—H | C—Br | E | 0.84 | 374, M − H$^+$ |
| B3 | H | H | C—H | C—Me | C—H | C—H | E | 0.83 | 312, M + H$^+$ |
| B4 | H | H | C—H | C—H | C—OMe | C—H | E | 0.77 | 328, M + H$^+$ |
| B5 | H | H | C—H | C—H | C—H | C—Me | E | 0.81 | 312, M + H$^+$ |

TABLE B-continued

Compounds of formula (I), more polar diastereoisomer (R2 = R3 = R5 = R7 = R8 = H, R6 = Me, W = O)

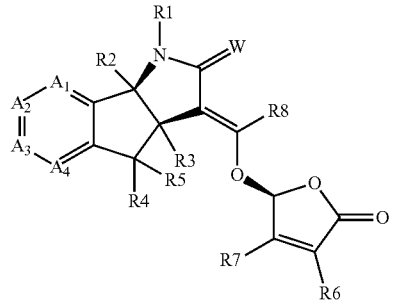

(I)

| Ex. | R1 | R4 | A$_1$ | A$_2$ | A$_3$ | A$_4$ | LCMS | RT | Mass |
|---|---|---|---|---|---|---|---|---|---|
| B6 | H | H | C—Br | C—H | C—H | C—H | E | 0.83 | 376, M + H$^+$ |
| B7 | H | H | C—H | C—H | C—H | C—CF$_3$ | E | 0.85 | 407, M + MeCN + H$^+$ |
| B8 | H | H | C—Me | C—H | C—H | C—H | E | 0.82 | 312, M + H$^+$ |
| B9 | H | H | C—H | C—H | C—F | C—H | E | 0.79 | 316, M + H$^+$ |
| B10 | H | H | C—H | C—H | C—Cl | C—H | E | 0.85 | 332, M + H$^+$ |
| B11 | H | H | C—H | C—H | C—H | C—CN | E | 0.70 | 364, M + MeCN + H$^+$ |
| B12* | H | H | C—CN | C—H | C—H | C—H | E | 0.72 | 364, M + MeCN + H$^+$ |
| B13 | H | H | C—$^n$Pr | C—H | C—H | C—H | E | 0.94 | 340, M + H$^+$ |
| B14 | H | H | C—H | C—H | C—H | C—$^n$Pr | E | 0.90 | 340, M + H$^+$ |
| B15* | Boc | H | C—H | C—H | C—H | C—H | B | 1.91 | 420, M + Na$^+$ |
| B16* | 2-(5-cyanopyridyl) | H | C—H | C—H | C—H | C—H | A | 1.82 | 400, M + H$^+$ |
| B17 | phenyl | H | C—H | C—H | C—H | C—H | A | 1.77 | 374, M + H$^+$ |
| B18 | 4-Cl-phenyl | H | C—H | C—H | C—H | C—H | A | 1.85 | 408, M + H$^+$ |
| B19* | 4-CF$_3$-phenyl | H | C—H | C—H | C—H | C—H | A | 1.90 | 442, M + H$^+$ |
| B20 | 4-OMe-phenyl | H | C—H | C—H | C—H | C—H | A | 1.75 | 404, M + H$^+$ |
| B21 | CO$_2$Et | H | C—H | C—H | C—H | C—H | A | 1.69 | 370, M + H$^+$ |
| B22 | Ac | H | C—H | C—H | C—H | C—H | A | 1.69 | 340, M + H$^+$ |
| B23 | Boc | H | C—H | NO2 | C—H | C—H | E | 0.98 | 477, M + Cl– |
| B24* | Boc | OAc | C—H | C—H | C—H | C—H | A | 1.82 | 478, M + Na$^+$ |
| B25* | Boc | F | C—H | C—H | C—H | C—H | A | 1.78 | 438, M + Na$^+$ |
| B26 | 2-thiazolyl | H | C—H | C—H | C—H | C—H | A | 1.80 | 381, M + H$^+$ |
| B27* | 4-F-benzyl | H | C—H | C—H | C—H | C—H | A | 1.85 | 406, M + H$^+$ |
| B28* | CH$_2$CN | H | C—H | C—H | C—H | C—H | A | 1.51 | 337, M + H$^+$ |
| B29* | allyl | H | C—H | C—H | C—H | C—H | A | 1.70 | 338, M + H$^+$ |

*1/1 mixture of diastereoisomers with the corresponding compound A.

TABLE C

Compounds of formula (IIb) (R2 = R3 = R4 = R5 = R8 = H, W = O)

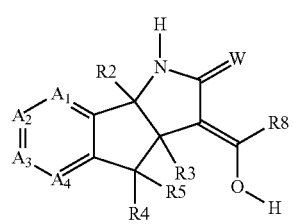

(IIb)

| Ex. | A$_1$ | A$_2$ | A$_3$ | A$_4$ | LCMS method | RT | Mass |
|---|---|---|---|---|---|---|---|
| C1 | C—H | C—H | C—H | C—H | A | 1.18 | 202, M + H$^+$ |
| C2 | C—H | C—H | C—H | C—Br | E | 0.72 | ES–; 280, M – H$^+$ |
| C3 | C—H | C—Me | C—H | C—H | E | 0.70 | 216, M + H$^+$ |
| C4 | C—H | C—H | OMe | C—H | E | 0.63 | ES–; 230, M – H$^+$ |
| C5 | C—H | C—H | C—H | C—Me | E | 0.68 | 216, M + H$^+$ |

TABLE C-continued

Compounds of formula (IIb) (R2 = R3 = R4 = R5 = R8 = H, W = O)

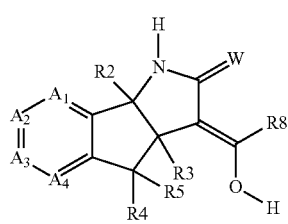

(IIb)

| Ex. | A$_1$ | A$_2$ | A$_3$ | A$_4$ | LCMS method | RT | Mass |
|---|---|---|---|---|---|---|---|
| C6 | C—Br | C—H | C—H | C—H | E | 0.70 | 278, M – H$^+$ |
| C7 | C—H | C—H | C—H | CN | E | 0.57 | ES–; 225, M – H$^+$ |
| C8 | C—CN | C—H | C—H | C—H | E | 0.59 | 227, M + H$^+$ |
| C9 | C—$^n$Pr | C—H | C—H | C—H | E | 0.81 | ES–; 242, M – H$^+$ |
| C10 | C—H | C—H | C—H | C—$^n$Pr | E | 0.80 | 244, M + H$^+$ |

TABLE C-continued

Compounds of formula (IIb) (R2 = R3 = R4 = R5 = R8 = H, W = O)

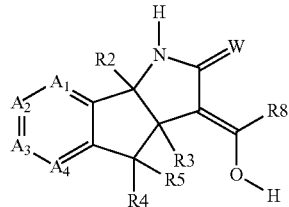

(IIb)

| Ex. | $A_1$ | $A_2$ | $A_3$ | $A_4$ | LCMS method | RT | Mass |
|---|---|---|---|---|---|---|---|
| C11 | C—H | C—H | C—H | C—$CF_3$ | E | 0.74 | ES−; 268, M − $H^+$ |
| C12 | C—Me | C—H | C—H | C—H | E | 0.68 | 216, M + $H^+$ |

TABLE C-continued

Compounds of formula (IIb) (R2 = R3 = R4 = R5 = R8 = H, W = O)

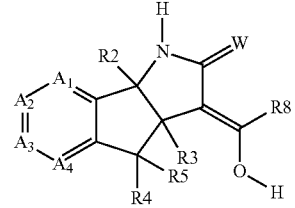

(IIb)

| Ex. | $A_1$ | $A_2$ | $A_3$ | $A_4$ | LCMS method | RT | Mass |
|---|---|---|---|---|---|---|---|
| C13 | C—H | C—H | C—F | C—H | E | 0.64 | 261, M + $CH_3CN$ + $H^+$ |
| C14 | C—H | C—H | C—Cl | C—H | E | 0.71 | ES−; 234, M − $H^+$ |

TABLE D

Compounds of formula (IIa) (W = O, R2 = R3 = R5 = R8 = H)

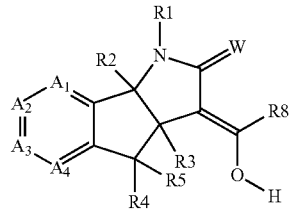

(IIa)

| Ex. | R1 | R4 | $A_1$ | $A_2$ | $A_3$ | $A_4$ | LCMS (method) | RT | Mass |
|---|---|---|---|---|---|---|---|---|---|
| D1 | Boc | H | C—H | C—H | C—H | C—H | A | 1.72 | 302, M + $H^+$ |
| D2 | Boc | H | C—H | C—H | C—H | C—Br | E | 0.98 | ES−; 380, M − $H^+$ |
| D3 | Boc | H | C—H | C—Me | C—H | C—H | E | 0.98 | ES−; 314, M − $H^+$ |
| D4 | Boc | H | C—H | C—H | OMe | C—H | E | 0.91 | ES−; 330, M − $H^+$ |
| D5 | Boc | H | C—H | C—H | C—H | C—Me | E | 0.97 | ES−; 314, M − $H^+$ |
| D6 | Boc | H | C—Br | C—H | C—H | C—H | E | 0.95 | ES−; 378, M − $H^+$ |
| D7 | Boc | H | C—H | C—H | C—H | C—CN | E | 0.86 | ES−; 325, M − $H^+$ |
| D8 | Boc | H | C—CN | C—H | C—H | C—H | E | 0.84 | ES−; 325, M − $H^+$ |
| D9 | Boc | H | C—$^n$Pr | C—H | C—H | C—H | E | 1.08 | ES−; 342, M − $H^+$ |
| D10 | Boc | H | C—H | C—H | C—H | C-Allyl | E | 1.02 | ES−; 340, M − $H^+$ |
| D11 | Boc | H | C—H | C—H | C—H | C—$^n$Pr | E | 1.06 | ES−; 342, M − $H^+$ |
| D12 | $CO_2Et$ | H | C—H | C—H | C—H | C—H | A | 1.53 | ES−; 272, M − $H^+$ |
| D13 | $CH_2CN$ | H | C—H | C—H | C—H | C—H | A | 1.37 | ES−; 239, M − $H^+$ |
| D14 | allyl | H | C—H | C—H | C—H | C—H | A | 1.50 | ES−; 240, M − $H^+$ |
| D15 | 2-thiazolyl | H | C—H | C—H | C—H | C—H | A | 1.59 | ES−; 283, M − $H^+$ |
| D16 | 2-(5-cyanopyridyl) | H | C—H | C—H | C—H | C—H | A | 1.65 | ES−; 302, M − $H^+$ |
| D17 | phenyl | H | C—H | C—H | C—H | C—H | A | 1.59 | ES+; 278, M + $H^+$ |
| D18 | 4-Cl-phenyl | H | C—H | C—H | C—H | C—H | A | 1.70 | ES+; 312, M + $H^+$ |
| D19 | 4-$CF_3$-phenyl | H | C—H | C—H | C—H | C—H | A | 1.77 | ES+; 346, M + $H^+$ |
| D20 | 4-OMe-phenyl | H | C—H | C—H | C—H | C—H | A | 1.59 | ES−; 306, M − $H^+$ |
| D21 | 4-F-Bn | H | C—H | C—H | C—H | C—H | A | 1.69 | ES−; 308, M − $H^+$ |
| D22 | Ac | H | C—H | C—H | C—H | C—H | A | 1.49 | ES−; 242, M − $H^+$ |
| D23 | Boc | H | C—H | C—NO2 | C—H | C—H | E | 1.69 | ES−; 345, M − $H^+$ |
| D24 | Boc | F | C—H | C—H | C—H | C—H | A | 1.65 | ES−; 318, M − $H^+$ |
| D25 | Boc | OAc | C—H | C—H | C—H | C—H | A | 1.68 | ES−; 358, M − $H^+$ |

TABLE E

Compounds of formula (IV) (W = O, R1 = Boc, R2 = R3 = R4 = R5 = H, R = Me)

(IV)

| Ex. | R4 | A₁ | A₂ | A₃ | A₄ | LCMS (method) | Retention (min.) | Mass |
|---|---|---|---|---|---|---|---|---|
| E1 | H | C—H | C—H | C—H | C—H | A | 1.78 | 329, M + H⁺ |
| E2 | H | C—H | C—Me | C—H | C—H | E | 1.02 | 343, M + H⁺ |
| E3 | H | C—H | C—H | C—OMe | C—H | E | 0.95 | 359, M + H⁺ |
| E4 | H | C—H | C—H | C—H | C—Me | E | 1.00 | 365, M + Na⁺ |
| E5 | H | C—H | C—H | C—H | C—CF₃ | E | 1.05 | 397, M + H⁺ |
| E6 | H | Me | C—H | C—H | C—H | E | 1.00 | 343, M + H⁺ |
| E7 | H | C—H | C—H | C—F | C—H | E | 0.96 | 369, M + Na⁺ |
| E8 | H | C—H | C—H | C—Cl | C—H | E | 1.03 | 363, M + H⁺ |
| E9 | H | C—H | C—H | C—H | C—Br | E | 1.02 | 308/310, M − Boc + H⁺ |
| E10 | H | C—Br | C—H | C—H | C—H | E | 0.97 | 837, 2M + Na⁺ |
| E11 | H | C—H | C—H | C—H | C—CN | E | 0.90 | 354, M + H⁺ |
| E12 | H | C—CN | C—H | C—H | C—H | E | 0.86 | 376, M + Na⁺ |
| E13 | H | C—ⁿPr | C—H | C—H | C—H | E | 1.11 | 371, M + H⁺ |
| E14 | H | C—H | C—H | C—H | C-Allyl | E | 1.05 | 369, M + H⁺ |
| E15 | OAc | C—H | C—H | C—H | C—H | A | 1.68 | 773, 2M + Na⁺ |

TABLE F

Compounds of formula (III) (R2 = R3 = R5 = H, W = O)

(III)

| Ex. | R1 | R4 | A₁ | A₂ | A₃ | A₄ | LCMS (method) | RT | Mass |
|---|---|---|---|---|---|---|---|---|---|
| F1 | Boc | H | C—H | C—H | C—H | C—H | B | 1.74 | 296, M + Na⁺ |
| F2 | Boc | H | C—H | C—Me | C—H | C—H | E | 1.01 | 597, 2M + H⁺ |
| F3 | Boc | H | C—H | C—H | C—OMe | C—H | E | 0.94 | 629, 2M + Na⁺ |
| F4 | Boc | H | C—H | C—H | C—H | C—Me | E | 0.99 | 351, M + MeCN + Na⁺ |
| F5 | Boc | H | C—H | C—H | C—H | C—CF₃ | E | 1.04 | 405, M + MeCN + Na⁺ |
| F6 | Boc | H | C—Me | C—H | C—H | C—H | E | 1.01 | 351, M + MeCN + Na⁺ |
| F7 | Boc | H | C—H | C—H | C—F | C—H | E | 0.95 | 605, 2M +Na⁺ |
| F8 | Boc | H | C—H | C—H | C—Cl | C—H | E | 1.01 | 371, M + MeCN + Na⁺ |
| F9 | Boc | H | C—H | C—H | C—H | C—Br | E | 1.02 | 725/727, 2M + Na⁺ |
| F10 | Boc | H | C—Br | C—H | C—H | C—H | E | 0.97 | 727, 2M + Na⁺ |
| F11 | Boc | H | C—H | C—H | C—H | CN | E | 0.87 | 619, 2M + Na⁺ |
| F12 | Boc | H | C—CN | C—H | C—H | C—H | E | 0.85 | 619, 2M + Na⁺ |
| F13 | Boc | H | C—H | C—H | C—H | C-Allyl | E | 1.06 | 377, M + MeCN + Na⁺ |
| F14 | Boc | H | C-Allyl | C—H | C—H | C—H | E | 1.06 | 377, M + MeCN + Na⁺ |
| F15 | Boc | H | C—ⁿPr | C—H | C—H | C—H | E | 1.14 | 338, M + Na⁺ |
| F16 | 4-Cl—Ph | H | C—H | C—H | C—H | C—H | A | 1.73 | 284, M + H⁺ |
| F17 | 4-OMe—Ph | H | C—H | C—H | C—H | C—H | A | 1.60 | 280, M + H⁺ |
| F18 | 4-CF₃—Ph | H | C—H | C—H | C—H | C—H | A | 1.80 | 318, M + H⁺ |
| F19 | Ph | H | C—H | C—H | C—H | C—H | A | 1.60 | 250, M + H⁺ |
| F20 | 2-(5-CN-pyridiyl) | H | C—H | C—H | C—H | C—H | A | 1.68 | 276, M + H⁺ |
| F21 | 2-thiazolyl | H | C—H | C—H | C—H | C—H | A | 1.66 | 257, M + H⁺ |
| F22 | Allyl | H | C—H | C—H | C—H | C—H | A | 1.51 | 214, M + H⁺ |
| F23 | 4-F-benzyl | H | C—H | C—H | C—H | C—H | A | 0.92 | 282, M + H⁺ |
| F24 | CNCH₂ | H | C—H | C—H | C—H | C—H | A | 1.33 | 213, M + H⁺ |
| F25 | CO₂Et | H | C—H | C—H | C—H | C—H | A | 1.52 | 246, M + H⁺ |
| F27 | Boc | OH | C—H | C—H | C—H | C—H | E | 0.78 | 601, 2M + Na⁺ |

TABLE F-continued

Compounds of formula (III) (R2 = R3 = R5 = H, W = O)

(III)

| Ex. | R1 | R4 | $A_1$ | $A_2$ | $A_3$ | $A_4$ | LCMS (method) | RT | Mass |
|---|---|---|---|---|---|---|---|---|---|
| F28 | Boc | F | C—H | C—H | C—H | C—H | A | 1.65 | 605, 2M + Na$^+$ |
| F29 | Boc | OAc | C—H | C—H | C—H | C—H | E | 0.90 | 685, 2M + Na$^+$ |
| F30 | Boc | H | C—H | C—NO$_2$ | C—H | C—H | E | 1.65 | 319, M + H$^+$ |

TABLE G

Compounds of formula (IIIa) (R2 = R3 = R4 = R5 = H, W = O)

(IIIa)

| Ex. | $A_1$ | $A_2$ | $A_3$ | $A_4$ | LCMS (method) | Retention (min.) | Mass |
|---|---|---|---|---|---|---|---|
| G1 | C—H | C—H | C—H | C—H | A | 1.17 | 174, M + H$^+$ |
| G2 | C—H | C—H | C—F | C—H | E | 0.64 | 192, M + H$^+$ |
| G3 | C—H | C—Me | C—H | C—H | E | 0.69 | 188, M + H$^+$ |
| G4 | C—H | C—H | C—OMe | C—H | E | 0.71 | 204, M + H$^+$ |
| G5 | C—H | C—H | C—H | C—Me | E | 0.70 | 188, M + H$^+$ |
| G6 | C—H | C—H | C—H | C—CF$_3$ | E | 0.76 | 242, M + H$^+$ |
| G7 | C—Me | C—H | C—H | C—H | E | 0.69 | 188, M + H$^+$ |
| G8 | C—H | C—H | C—Cl | C—H | E | 0.71 | 208, M + H$^+$ |
| G9 | C—H | C—H | C—H | C—Br | A | 1.43 | 252/254 M + H$^+$ |
| G10 | C—Br | C—H | C—H | C—H | E | 0.69 | 252/254 M + H$^+$ |

TABLE H

Compounds of formula (VI) (R3 = R4 = R5 = H, W = O)

(VI)

| Ex. | R | $A_1$ | $A_2$ | $A_3$ | $A_4$ | LCMS (method and column) | RT | Mass |
|---|---|---|---|---|---|---|---|---|
| H1 | Me | C—H | C—H | C—H | C—H | A | 1.40 | 205 M + H$^+$ |
| H2 | Me | C—H | C—H | C—F | C—H | C (Gemini NX C18, 50 × 4.6 mm, 5 u, 110 Angström) | 5.51 | 223 M + H$^+$ |
| H3 | Et | C—H | C—Me | C—H | C—H | D | 3.28 | 241 M + Na$^+$ |
| H4 | Et | C—H | C—H | C—OMe | C—H | D | 2.95 | 257 M + Na$^+$ |
| H5 | Et | C—H | C—H | C—H | C—Me | D | 3.20 | 241 M + Na$^+$ |

TABLE H-continued

Compounds of formula (VI) (R3 = R4 = R5 = H, W = O)

$$(VI)$$

| Ex. | R | $A_1$ | $A_2$ | $A_3$ | $A_4$ | LCMS (method and column) | RT | Mass |
|---|---|---|---|---|---|---|---|---|
| H6 | Me | C—H | C—H | C—H | C—$CF_3$ | C (Reprosil C18, 50 × 4.6 mm, 5 um, 100 Angström) | 3.71 | 273 M + H$^+$ |
| H7 | Me | C—Me | C—H | C—H | C—H | C (Zorbax Ext C18, 5 um, 110 Angström, 50 × 4.6 mm) | 4.02 | 219 M + H$^+$ |
| H8 | Me | C—H | C—H | C—Cl | C—H | C (Xbridge C18, 50 × 4.6 mm, 5 u, 110 Angström) | 4.84 | 239 M + H$^+$ |
| H9 | Et | C—H | C—H | C—H | C—Br | A | 1.11 | 297/299 M + H$^+$ |
| H10 | Et | C—Br | C—H | C—H | C—H | E | 0.90 | 297/299 M + H$^+$ |

Biological Examples

The effect of compounds of formula (I) on germination of *Orobanche cumana* Wallr. seeds was evaluated on glass fiber filter paper (GFFP) in petri dishes. Seeds were preconditioned at moisture and suitable temperature to become responsive to the specific chemical germination stimulants.

Test compounds were dissolved in DMSO (10 000 mg l$^{-1}$) and stored at room temperature in a desiccators with desiccants. The stock solutions were dissolved with deionised water to the appropriate final test concentration.

Seeds of *O. cumana* race 'F' were collected from sunflower fields in Manzanilla (Seville, Spain) in 2006 (seed lot IN146) and 2008 (seed lot IN153) and stored at room temperature. To separate seeds from heavy organic debris, a modified sucrose floatation technique as described by Hartman & Tanimonure (Plant Disease (1991), 75, p. 494) was applied. Seeds were filled into a separation funnel and stirred in water. When seeds floated to the surface, the water fraction containing heavy debris was discarded. Seeds were re-suspended in 2.5M sucrose solution (specific gravity of 1.20) and heavy debris was allowed to settle down for 60 min. After removing debris, seeds were disinfected in 1% sodium hypochlorite solution and 0.025% (v/v) Tween 20 for 2 min. The seeds were decanted onto two layers of cheesecloth, rinsed with sterile deionised water and re-suspended in sterile deionised water. Two ml of the seed suspension containing approximately 150-400 seeds were spread evenly on two layers of sterile glass fiber filter paper disc (Ø9 mm) in Petri dishes (Ø9 cm). After wetting the discs with 3 ml sterile deionised water, petri dishes were sealed with parafilm. Seeds were incubated for 10 days at 20° C. in the dark for seed conditioning. The upper disc with conditioned seeds was briefly dried, transferred to a petri dish lined with a dry GFFP disc, and wetted with 6 ml of the appropriate test solution. The compounds of formula (I) were tested at concentrations of 0.001, 0.01, and 0.1 mg l$^{-1}$. The strigolactone analogue GR24 (commercially available as a mixture of isomers) was included as positive control and 0.001% DMSO as negative control. All treatments were tested in five replicates. Seeds were re-incubated at 20° C. in the dark and examined for germination 10 days later. The radicles of germinated seeds were stained for 5 min with blue ink (MIGROS, Switzerland) in 5% acetic acid according to Long et al. (Seed Science Research (2008), 18, p. 125). After staining, seeds were scanned using a flatbed scanner with an optical resolution of 1200 dpi (PULSTEK, OpticPro ST28) or photographed using a camera stand mounted with a digital SLR camera (Canon EOS 5D). Germination of 100 seeds per replicate was evaluated on digital images. Seeds were considered germinated when the radicle protruded from the seed coat. SAS statistical software package version 9.1 was used for analysis of variance (GLM procedure) and multiple comparisons of treatment means (Sidak t-test) based on arcsine transformed percentage germination data. The results of the *Orobanche* seed germination tests are shown in Table 3-8.

The results show that all compounds tested showed a germination inducing effect compared to the untreated control.

TABLE 3

Effect of compounds of formula (I) on germination of preconditioned *Orobanche cumana* seeds of seed lot IN146 raceF.

| Compound | Concentration (mg l$^{-1}$) | Germination (%)* | |
|---|---|---|---|
| None (Control, 0.001% DMSO) | 0 | 0 | e |
| P1 | 0.001 | 70.5 | a b |
|  | 0.01 | 83.7 | a |
|  | 0.1 | 83.1 | a |
| P3 | 0.001 | 68 | a b c |
|  | 0.01 | 82.4 | a |
|  | 0.1 | 84 | a |
| GR24 | 0.001 | 25.9 | d |
|  | 0.01 | 44.9 | d c |
|  | 0.1 | 59.8 | b c |

*Mean; N = 5 × 100 seeds; re-transformed data are shown

Means with the same letter are not significantly different, P ≤ 0.05

TABLE 4

Germination (%) of preconditioned *Orobanche cumana* seeds of lot IN146, raceF treated with compounds of formula (I) at different concentrations.

| Compound | Germination %[#] at concentration of | | |
|---|---|---|---|
| | 0.1 mg l⁻¹ | 0.01 mg l⁻¹ | 0.001 mg l⁻¹ |
| A5 | 85.5 ab | 90 a | 74.5 abc |
| A6 | 27.8 bcde | 59.2 abcd | 22.3 cde |
| A10 | 85.1 ab | 84.0 ab | 81.3 abc |
| A12* | 32 bcde | 4.2 e | 0 e |
| A13 | 21.5 cde | 64.5 abcd | 14.3 de |

*1/1 mixture of diastereoisomers with the corresponding compound B.
[#]Mean; N = 5 × 100 seeds; re-transformed data are shown
Means with the same letter are not significantly different, $P \leq 0.05$
Means with letter 'e' are not significantly different from aqueous control (0.001% DMSO) showing 0% germination.

TABLE 5

Germination (%) of preconditioned *Orobanche cumana* seeds of lot IN146, raceF treated with compounds of formula (I) at different concentrations.

| Compound | Germination %[#] at concentration of | | |
|---|---|---|---|
| | 0.1 mg l⁻¹ | 0.01 mg l⁻¹ | 0.001 mg l⁻¹ |
| A2 | 83.2 ab | 82 ab | 76.9 abc |
| A11 | 85.5 ab | 88.4 ab | 86.3 ab |
| A14 | 86.2 ab | 91.5 a | 85.3 ab |
| A15* | 25 d | 12.4 de | 0 e |
| GR-24 | 45.9 bcd | 33.3 cd | 21.2 de |

*1/1 mixture of diastereoisomers with the corresponding compound B.
[#]Mean; N = 5 × 100 seeds; re-transformed data are shown
Means with the same letter are not significantly different, $P \leq 0.05$
Means with letter 'e' are not significantly different from aqueous control (0.001% DMSO) showing 0% germination.

TABLE 6

Germination (%) of preconditioned *Orobanche cumana* seeds of lot IN146, raceF treated with compounds of formula (I) at different concentrations.

| Compound | Germination %[#] at concentration of | | |
|---|---|---|---|
| | 0.1 mg l⁻¹ | 0.01 mg l⁻¹ | 0.001 mg l⁻¹ |
| A7 | 91.1 ab | 93.5 a | 87.5 ab |
| A8 | 69.9 bc | 84.4 abc | 72.9 bc |
| A9 | 71.5 bc | 85.2 abc | 90.2 ab |
| GR-24 | 86.6 ab | 61.4 c | 17.5 d |

[#]Mean; N = 5 × 100 seeds; re-transformed data are shown
Means with the same letter are not significantly different, $P \leq 0.05$
Means with letter 'e' are not significantly different from aqueous control (0.001% DMSO) showing 0% germination.

TABLE 7

Germination (%) of preconditioned *Orobanche cumana* seeds of lot IN153 raceF treated with compounds of formula (I) at different concentrations.

| Compound | Germination %[#] at concentration of | | |
|---|---|---|---|
| | 0.1 mg l⁻¹ | 0.01 mg l⁻¹ | 0.001 mg l⁻¹ |
| A1 | 97.5 a | 95.2 ab | 98.1 a |
| A3 | 98.0 a | 98.5 a | 96.4 ab |
| A4 | 99.0 a | 95.8 ab | 98.9 a |
| A17 | 99.4 a | 98.9 a | 99.2 a |
| A18 | 99.1 a | 99.1 a | 89.8 ab |

TABLE 7-continued

Germination (%) of preconditioned *Orobanche cumana* seeds of lot IN153 raceF treated with compounds of formula (I) at different concentrations.

| Compound | Germination %[#] at concentration of | | |
|---|---|---|---|
| | 0.1 mg l⁻¹ | 0.01 mg l⁻¹ | 0.001 mg l⁻¹ |
| A20 | 89.3 ab | 14.4 c | 2.0 c |
| A23 | 98.0 a | 98.9 a | 63.2 b |
| A25* | 86.3 ab | 14.3 c | 1.2 c |
| GR-24 | 96.2 ab | 97.2 a | 89.5 ab |

*1/1 mixture of diastereoisomers with the corresponding compound B.
[#]Mean; N = 5 × 100 seeds; re-transformed data are shown
Means with the same letter are not significantly different, $P \leq 0.05$
Means with letter 'd' are not significantly different from aqueous control (0.001% DMSO) showing 0% germination

TABLE 8

Germination (%) of preconditioned *Orobanche cumana* seeds of lot IN153, raceF treated with compounds of formula (I) at different concentrations.

| Compound | Germination %[#] at concentration of | | |
|---|---|---|---|
| | 0.1 mg l⁻¹ | 0.01 mg l⁻¹ | 0.001 mg l⁻¹ |
| A1 | 95.5 ab | 94.6 abc | 95.7 ab |
| A16* | 88.2 abc | 60.6 cde | 7.8 fg |
| A19* | 96.4 a | 92.2 abc | 71.5 abcde |
| A21 | 96.7 a | 93.4 abc | 83.7 abcde |
| A22 | 95.7 ab | 95.3 ab | 87.6 abc |
| A24* | 96.8 a | 86.4 abcd | 44.8 def |
| A26 | 93.9 abc | 95.4 ab | 93.9 abc |
| A27* | 80.1 abcde | 63.3 abcde | 7.7 fg |
| A28* | 96.3 ab | 89.2 abc | 42.4 ef |
| A29* | 94.0 abc | 94.5 abc | 90.3 abc |
| GR-24 | 97.0 a | 94.1 abc | 84.1 abcde |

*1/1 mixture of diastereoisomers with the corresponding compound B.
[#]Mean; N = 5 × 100 seeds; re-transformed data are shown
Means with the same letter are not significantly different, $P \leq 0.05$
Means with letter 'g' are not significantly different from aqueous control (0.001% DMSO) showing 0.3% germination

The invention claimed is:

1. A compound of formula (I)

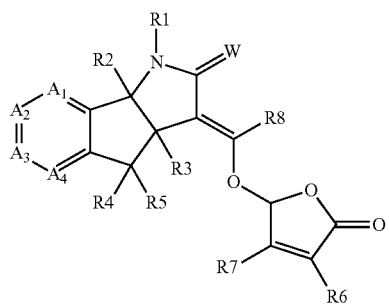

wherein

W is O or S;

R2 and R3 are independently hydrogen or C1-C3 alkyl;

R4 and R5 are independently hydrogen, halogen, nitro, cyano, C1-C3 alkyl, C1-C3 haloalkyl, C1-C3 alkoxy, hydroxyl, —OC(O)R9, amine, N—C1-C3 alkyl amine or N,N-di-C1-C3 alkyl amine;

R9 is hydrogen, C1-C6 alkyl, C1-C6 alkoxy or C1-C6 haloalkyl;

R6 and R7 are independently hydrogen, C1-C3 alkyl, hydroxyl or C1-C3 alkoxy;

R8 is hydrogen, nitro, cyano, C1-C6 alkyl or C1-C6 haloalkyl;

R1 is hydrogen, C1-C6 alkoxy, hydroxyl, amine, N—C1-C6 alkyl amine, N,N-di-C1-C6 alkyl amine, C1-C6 alkyl substituted or not by one to five R10, C1-C8 alkylcarbonyl, C1-C8 alkoxycarbonyl, aryl, aryl substituted by one to five R10, heteroaryl, heteroaryl substituted by one to five R10, heterocyclyl, heterocyclyl substituted by one to five R10, benzyl, or benzyl substituted by one to five R10;

R10 is hydrogen, cyano, nitro, halogen, C1-C6 alkyl, C1-C6 alkoxy, C1-C6 haloalkyl, C2-C6 alkenyl, or C2-C6 alkynyl;

$A_1, A_2, A_3$ and $A_4$ are each independently C—X or nitrogen, wherein each X may be the same or different, and provided that no more than two of $A_1, A_2, A_3$ and $A_4$ are nitrogen; and X is hydrogen, halogen, cyano, C1-C3 hydroxyalkyl, —OC(O)R9, C1-C6 alkoxy, C1-C6 alkyl or C1-C6 haloalkyl, nitro, amine, N—C1-C6 alkyl amine, N,N-di-C1-C6 alkyl amine or NHC(O)R9;

or salts or N-oxides thereof.

2. A compound according to claim 1, wherein W is O.

3. A compound according to claim 2, wherein

R2 and R3 are independently hydrogen, methyl or ethyl;

R4 and R5 are independently hydrogen, hydroxyl, methyl or ethyl;

R6, R7 and R8 are independently hydrogen, methyl or ethyl;

R1 is hydrogen, C1-C6 alkoxy, C1-C6 alkyl substituted or not by one to five R10, C1-C8 alkylcarbonyl, C1-C8 alkoxycarbonyl, aryl, aryl substituted by one to five R10, heteroaryl, heteroaryl substituted by one to five R10, heterocyclyl, heterocyclyl substituted by one to five R10, benzyl, or benzyl substituted by one to five R10;

R10 is independently hydrogen, cyano, nitro, halogen, C1-C6 alkyl, C1-C6 alkoxy or C1-C6 haloalkyl;

$A_1, A_2, A_3$ and $A_4$ are each independently C—X; and

X is hydrogen, hydroxyl, halogen, cyano, methyl, ethyl, n-propyl, hydroxymethyl, trifluoromethyl or methoxy.

4. A plant growth regulator or seed germination promoting composition, comprising a compound according to claim 1, and an agriculturally acceptable formulation adjuvant.

5. A method for regulating the growth of plants at a locus, wherein the method comprises applying to the locus a plant growth regulating amount of a composition according to claim 4.

6. A method for promoting the germination of seeds comprising applying to the seeds, or a locus containing seeds, a seed germination promoting amount of a composition according to claim 4.

7. A method for controlling weeds comprising applying to a locus containing weed seeds a seed germination promoting amount of a composition according to claim 4, allowing the seeds to germinate, and then applying to the locus a post-emergence herbicide.

8. A method for making a compound of formula (I)

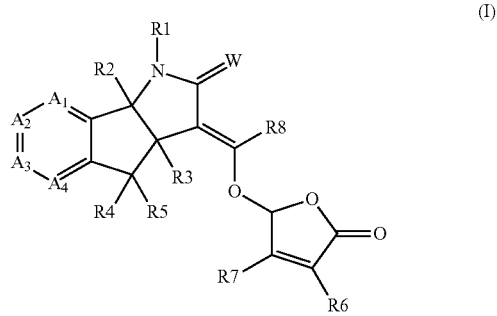

comprising the steps of:

a) treating a compound of formula (VI)

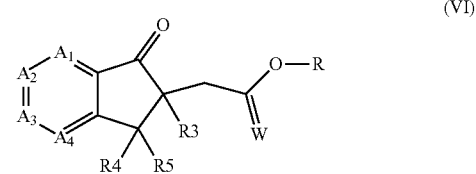

with an amine derivative, followed by reduction to give a compound of formula (III);

b) treating the compound of formula (III)

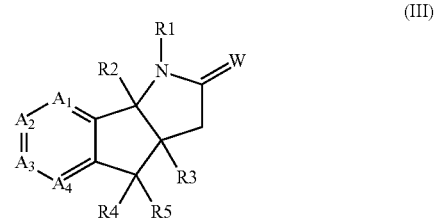

with a formic ester derivative under basic conditions to form a compound of formula (II); and c) treating the compound of formula (II)

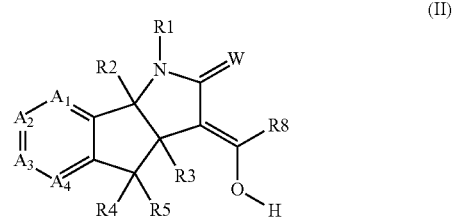

with a 5H-furanone derivative

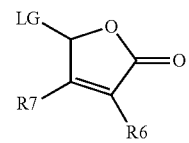

under basic conditions; wherein W is O or S; R2 and R3 are independently hydrogen or C1-C3 alkyl; R4 and R5 are independently hydrogen, halogen, nitro, cyano, C1-C3 alkyl, C1-C3 haloalkyl, C1-C3 alkoxy, hydroxyl, —OC(O)R9, amine, N—C1-C3 alkyl amine or N,N-di-C1-C3 alkyl amine; R9 is hydrogen, C1-C6 alkyl, C1-C6 alkoxy or C1-C6 haloalkyl; R6 and R7 are independently hydrogen, C1-C3 alkyl, hydroxyl or C1-C3 alkoxy; R8 is hydrogen, nitro, cyano, C1-C6 alkyl or C1-C6 haloalkyl; R1 is hydrogen, C1-C6 alkoxy, hydroxyl, amine, N—C1-C6 alkyl amine, N,N-di-C1-C6 alkyl amine, C1-C6 alkyl substituted or not by one to five R10, C1-C8 alkylcarbonyl, C1-C8 alkoxycarbonyl, aryl, aryl substituted by one to five R10, heteroaryl, heteroaryl substituted by one to five R10, heterocyclyl, heterocyclyl substituted by one to five R10, benzyl, or benzyl substituted by one to five R10; R10 is hydrogen, cyano, nitro, halogen, C1-C6 alkyl, C1-C6 alkoxy, C1-C6 haloalkyl, C2-C6 alkenyl, or C2-C6 alkynyl; $A_1$, $A_2$, $A_3$ and $A_4$ are each independently C—X or nitrogen, wherein each X may be the same or different, and provided that no more than two of $A_1$, $A_2$, $A_3$ and $A_4$ are nitrogen; and X is hydrogen, halogen, cyano, C1-C3 hydroxyalkyl, —OC(O)R9, C1-C6 alkoxy, C1-C6 alkyl or C1-C6 haloalkyl, nitro, amine, N—C1-C6 alkyl amine, N,N-di-C1-C6 alkyl amine or NHC(O)R9 and LG represents a leaving group.

9. A compound of formula (II)

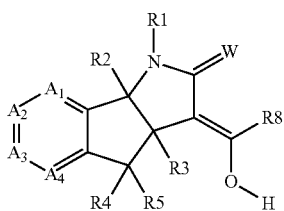

(II)

wherein

W is O or S;

R2 and R3 are independently hydrogen or C1-C3 alkyl;

R4 and R5 are independently hydrogen, halogen, nitro, cyano, C1-C3 alkyl, C1-C3 haloalkyl, C1-C3 alkoxy, hydroxyl, —OC(O)R9, amine, N—C1-C3 alkyl amine or N,N-di-C1-C3 alkyl amine;

R9 is hydrogen, C1-C6 alkyl, C1-C6 alkoxy or C1-C6 haloalkyl;

R8 is hydrogen, nitro, cyano, C1-C6 alkyl or C1-C6 haloalkyl;

R1 is hydrogen, C1-C6 alkoxy, hydroxyl, amine, N—C1-C6 alkyl amine, N,N-di-C1-C6 alkyl amine, C1-C6 alkyl substituted or not by one to five R10, C1-C8 alkylcarbonyl, C1-C8 alkoxycarbonyl, aryl, aryl substituted by one to five R10, heteroaryl, heteroaryl substituted by one to five R10, heterocyclyl, heterocyclyl substituted by one to five R10, benzyl, or benzyl substituted by one to five R10;

R10 is hydrogen, cyano, nitro, halogen, C1-C6 alkyl, C1-C6 alkoxy, C1-C6 haloalkyl, C2-C6 alkenyl, or C2-C6 alkynyl;

$A_1$, $A_2$, $A_3$ and $A_4$ are each independently C—X or nitrogen, wherein each X may be the same or different, and provided that no more than two of $A_1$, $A_2$, $A_3$ and $A_4$ are nitrogen; and X is hydrogen, halogen, cyano, C1-C3 hydroxyalkyl, —OC(O)R9, C1-C6 alkoxy, C1-C6 alkyl or C1-C6 haloalkyl, nitro, amine, N—C1-C6 alkyl amine, N,N-di-C1-C6 alkyl amine or NHC(O)R9;

or salts or N-oxides thereof.

* * * * *